United States Patent
Muller-Feuga et al.

(10) Patent No.: US 9,663,749 B2
(45) Date of Patent: *May 30, 2017

(54) REACTION CASING FOR A PHOTOSYNTHETIC REACTOR AND ASSOCIATED PHOTOSYNTHETIC REACTOR

(71) Applicant: MICROPHYT, Baillargues (FR)

(72) Inventors: Arnaud Muller-Feuga, Baillargues (FR); Michel Lemar, Saint Symphorien d'Ozon (FR)

(73) Assignee: MICROPHYT, Baillargues (FR)

(*) Notice: Subject to any disclaimer, the term of this patent is extended or adjusted under 35 U.S.C. 154(b) by 160 days.

This patent is subject to a terminal disclaimer.

(21) Appl. No.: 14/359,267

(22) PCT Filed: Nov. 13, 2012

(86) PCT No.: PCT/FR2012/052610
§ 371 (c)(1),
(2) Date: May 19, 2014

(87) PCT Pub. No.: WO2013/072614
PCT Pub. Date: May 23, 2013

(65) Prior Publication Data
US 2014/0335598 A1   Nov. 13, 2014

(30) Foreign Application Priority Data
Nov. 17, 2011 (FR) ...................................... 11 60480

(51) Int. Cl.
C12M 1/00 (2006.01)
C12M 1/09 (2006.01)
C12N 1/12 (2006.01)

(52) U.S. Cl.
CPC ............ *C12M 21/02* (2013.01); *C12M 23/56* (2013.01); *C12N 1/12* (2013.01); *Y10T 29/49826* (2015.01)

(58) Field of Classification Search
CPC .......... C12M 21/02; C12M 23/56; C12N 1/12
See application file for complete search history.

(56) References Cited

U.S. PATENT DOCUMENTS 3,955,317 A      5/1976  Gudin
4,868,123 A  *  9/1989  Berson et al. ......... C12M 21/02
                                                              210/149

(Continued)

FOREIGN PATENT DOCUMENTS

ES    2150389 A1    11/2000
ES    2193860 A1    11/2003

(Continued)

OTHER PUBLICATIONS

International Search Report issued Mar. 7, 2013 re: PCT/FR2012/052610; citing: GB 2 473 864 A, WO 2010/012028 A1, US 3 955 317 A, WO 2009/051479 A2 and WO 2011/058267 A2.

(Continued)

*Primary Examiner* — Gautam Prakash
(74) *Attorney, Agent, or Firm* — Cantor Colburn LLP

(57) ABSTRACT

Reaction casing (1) for a photosynthetic reactor suitable for cultivating photosynthetic microorganisms, in particular algae, said reaction casing (1) being designed for both floating on an expanse of water and defining a path for a gas/liquid culture medium to flow in two phases between a first and a second opening (11, 12) of said casing. The casing comprises, on the one hand, an upper membrane (31) and a lower membrane (32) made at least partially of a flexible material, hermetically sealed and transparent to light radiation, said membranes being hermetically connected to one another by connecting lines (41, 42) defining inflatable cells (Continued)

(33, 34) and, on the other hand, connection elbows (35, 36) joining said cells in pairs to define the course of flow in a generally sinuous form, one of the cells (33) being fluidly linked to the first opening and another cell (34) being fluidly linked to the second opening (12). The present invention is applicable in the field of photosynthetic microorganism cultivation, in particular algae cultivation.

19 Claims, 9 Drawing Sheets

(56) References Cited

U.S. PATENT DOCUMENTS

| | | | | |
|---|---|---|---|---|
| 6,370,815 | B1* | 4/2002 | Skill et al. | C12M 21/02 435/298.1 |
| 8,822,199 | B2* | 9/2014 | Muller-Feuga et al. | C12M 21/02 156/213 |
| 2008/0178739 | A1* | 7/2008 | Lewnard et al. | C12M 21/02 95/186 |
| 2010/0285575 | A1* | 11/2010 | Michiels | C12M 21/02 435/289.1 |
| 2011/0092726 | A1* | 4/2011 | Clarke | C12M 21/02 554/175 |
| 2011/0124087 | A1* | 5/2011 | Meiser et al. | C12M 21/02 435/243 |
| 2011/0217692 | A1* | 9/2011 | Morgan et al. | C12M 21/02 435/3 |
| 2011/0281340 | A1* | 11/2011 | Turner et al. | C12M 21/02 435/257.1 |

FOREIGN PATENT DOCUMENTS

| | | |
|---|---|---|
| FR | 2324224 A1 | 4/1977 |
| FR | 2361060 A1 | 3/1978 |
| FR | 2621232 A1 | 4/1989 |
| FR | 2621323 | 4/1989 |
| FR | 2685344 A1 | 6/1993 |
| FR | 2875511 A3 | 3/2006 |
| GB | 2118572 A | 11/1983 |
| GB | 2331762 A | 6/1999 |
| GB | 2473865 A | 3/2011 |
| WO | 2008134010 A2 | 11/2008 |
| WO | 2009051479 A2 | 4/2009 |
| WO | 2009090549 A2 | 7/2009 |
| WO | 2010012028 A1 | 2/2010 |
| WO | 2011058267 A2 | 5/2011 |

OTHER PUBLICATIONS

Written Opinion issued Mar. 7, 2013 re: PCT/FR2012/052610; pp. 5; citing: GB 2 473 865 A, WO 2010/012028 A1, US 3 955 317 A.

* cited by examiner

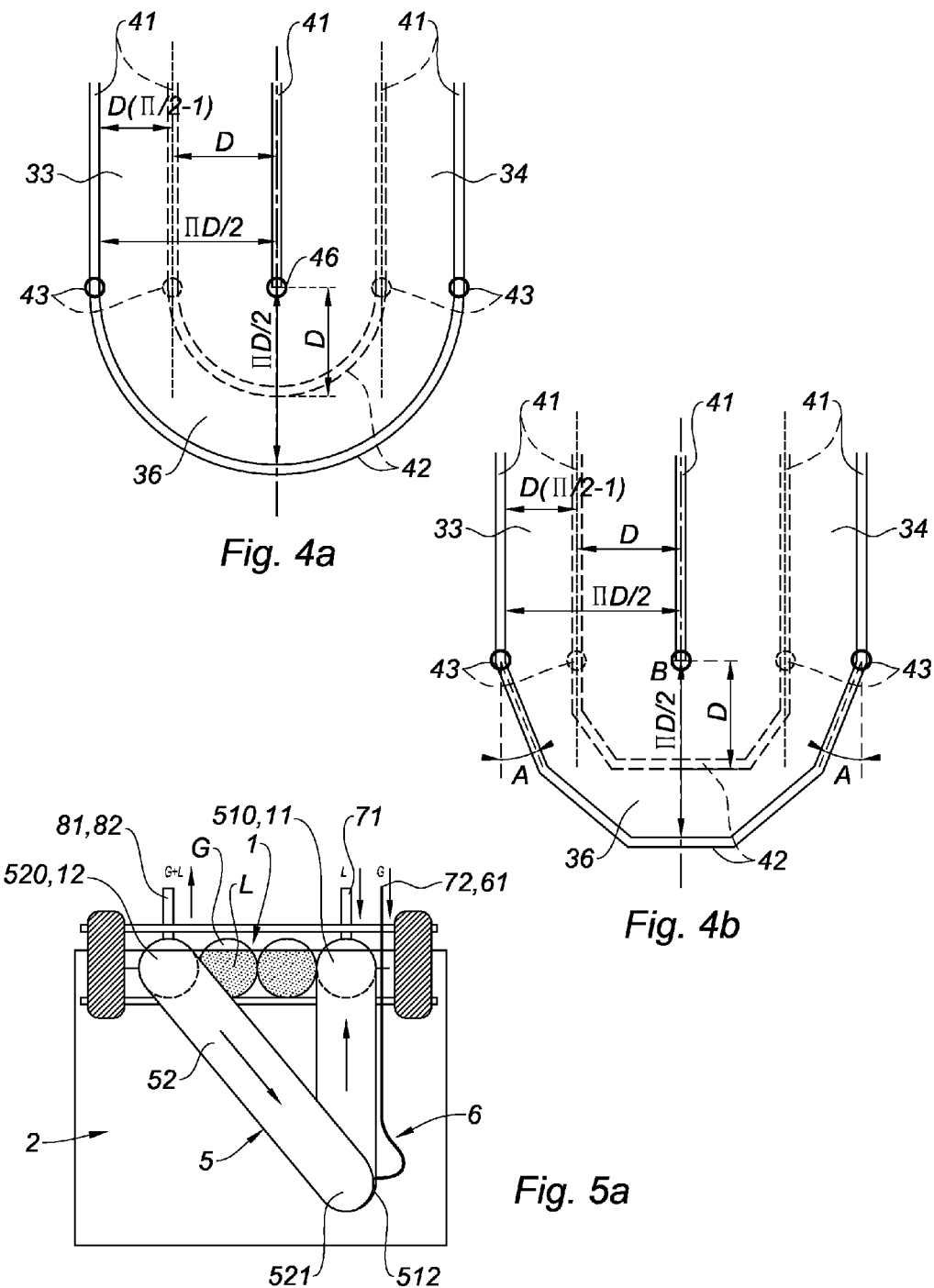

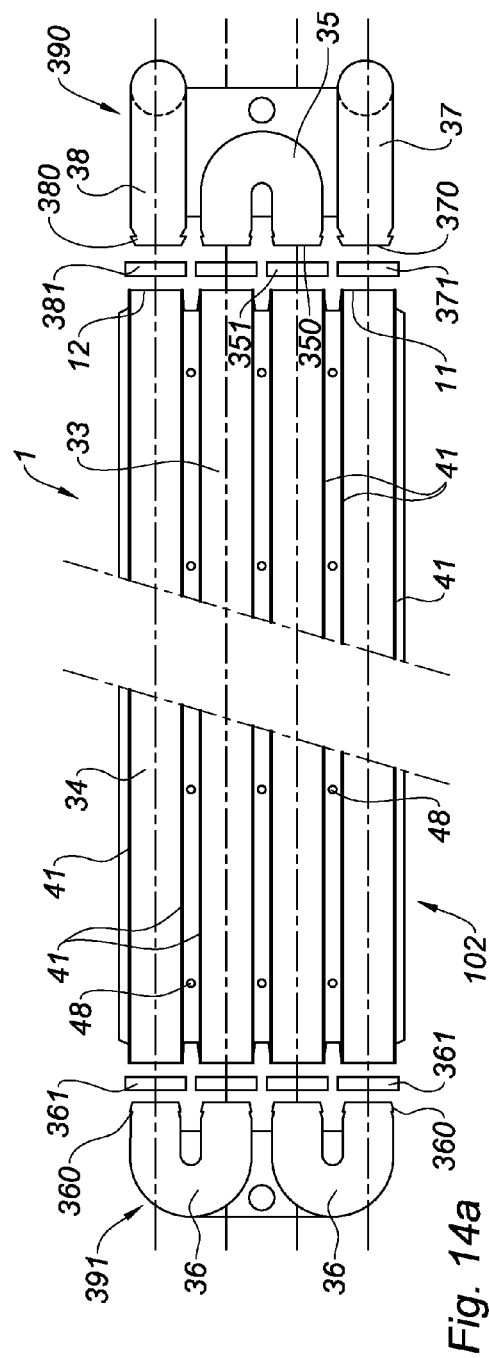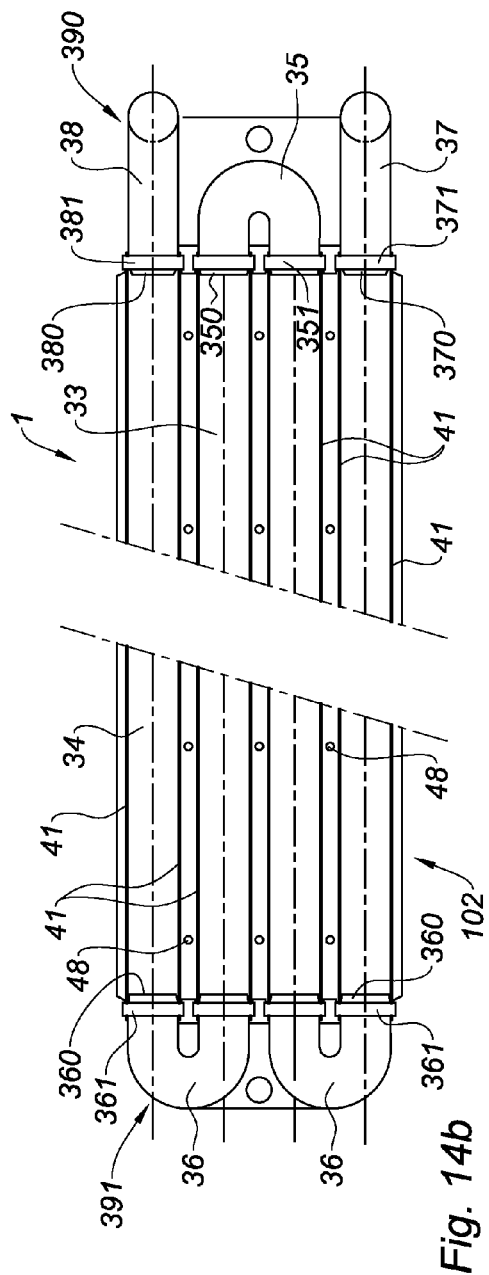
Fig. 14a
Fig. 14b

REACTION CASING FOR A PHOTOSYNTHETIC REACTOR AND ASSOCIATED PHOTOSYNTHETIC REACTOR

TECHNICAL FIELD

The present invention relates to a reaction casing for a photosynthetic reactor suitable for cultivating photosynthetic microorganisms, in particular algae, to a manufacturing method of such a casing, to an associated photosynthetic reactor and also to an associated photosynthetic microorganism cultivation method.

It relates in particular to a reaction casing designed, on one hand, to float on an expanse of water and, on the other hand, to delimit a two-phase flow pathway for a gas/liquid culture medium between two openings of said casing.

The present invention applies to the cultivation of any aquatic photosynthetic organism of small size, that is to say, all life-forms capable of development and photosynthesis in an appropriate nutritive culture medium, in the presence of solar radiation and carbon-rich gas, such as carbon dioxide, microalgae being the main representatives of this life-form.

Amongst the photosynthetic microorganisms related to the invention are, in particular, aquatic plants such as for example microalgae, moss protonemas, small macroalgae and isolated cells of multicellular plants. These aquatic plants have interesting properties in particular in the fields of pharmacy, of human and animal nutrition, of dermo-cosmetology, of energy and of the environment.

BACKGROUND

Like most photosynthetic microorganisms, the access to this resource consists essentially in the assisted culture in the suitable reactors. Light being their main substrate, the culture medium must have an optical interface receiving a light flux. The difficulty of cultivating photosynthetic microorganisms resides in that they are themselves obstacles to the passage of light which is their main substrate. The culture growth will therefore stabilize when light will no more penetrate the thickness of culture. This phenomenon is called self-shadowing.

The length of the optical path, or "light path length", varying generally between a few centimeters and a few decimeters, allows to characterize of the different modes of containment, and to determine essentially the biomass production per unit time and unit optical area (surface productivity in $g/m^2/day$) and the culture concentration ($g/L$) in the final growth phase.

The photosynthesis reaction is also accompanied by a consumption of carbon dioxide ($CO_2$) and a production of oxygen ($O_2$). The excess of oxygen inhibits the reaction, while the absence of carbon dioxide interrupts it by lack of substrate to be transformed. A gas/liquid interface therefore must be arranged for the mass transfers between these gases and the liquid phase. In order to promote these exchanges and avoid the heterogeneities, the culture must hold a mixture intended to renew organisms at the aforementioned optical interface and also at the gas/liquid interface.

It is well known, particularly in GB 2 118 572 A, ES 2 193 860 A1, GB 2 331 762 A, ES 2 150 389 A1, FR 2 685 344 A1 and FR 2 875 511 A3, to use closed photosynthetic reactors comprising a closed loop within which the liquid culture medium circulates, said closed loop comprising a reaction pipe provided with reaction sections made from a material transparent to light radiation, and a closing pipe ensuring the connection between the two opposite ends of the reaction pipe.

The reaction pipe of photobioreactors generally consists of horizontal transparent tubes, made of glass or plastic material, with a thickness or a diameter in the order of a few centimeters, which are end-to-end connected by elbows and collectors to form together a single coil-shaped pipe or parallel back-and-forth pins.

The closing pipe comprises a vertical tube called ascending wherein the liquid medium moves upward, and a vertical tube called descending wherein the liquid medium moves downward in particular due to gravity.

The gas injection system generally implemented in photobioreactors consists of an airlift, otherwise said "gas-lift" or gas lift device, that is to say a gas injection at the base of the ascending vertical tube of the closing pipe; said gas injection being used to both put into circulation the liquid reaction medium and to perform gas-liquid exchanges. The airlift includes in its upper portion a head or an enlarged volume tank wherein lower circulation speeds allow gas-liquid separation, and the descending vertical tube of the closing pipe opens into the bottom of the head tank to feed the reaction pipe with liquid.

The aforementioned photobioreactors apply the principle according to which the reaction takes place only in the liquid phase, in other words these photobioreactors seek to minimize the volume of gas injected into the reactor so as not to decrease accordingly the volume of liquid culture medium, in order not to reduce production. Thus, in these photobioreactors, the extraction of oxygen is often performed by means of an ascending vertical closing tube defined hereinabove; said ascending vertical tube forming a bubble column opening into the head tank receiving the liquid culture medium, and including a gas injection in the lower portion, opportunely, of $CO_2$-enriched air. As described hereinabove, the two functions of circulation and gas transfer are combined within this unique device, called airlift, which creates an ascending vertical circulation by momentum exchange between the liquid mass and the gas bubbles resulting from the injection. The photosynthetic oxygen in supersaturation in the liquid passes into the gas phase by air sweeping, while the $CO_2$ passes into solution. These degassing and carbonatation functions are indispensable and intervene simultaneously and inseparably at this unique device wherein the culture must pass according to a high frequency in order to avoid adeleterious increase in the dissolved oxygen content.

The airlifts have the drawback of generating gas bubbles that move upward within the ascending vertical tube of the photobioreactor closing pipe. Indeed, the Applicant has observed the deleterious role of these bubbles for the cultivation of microorganisms in the photobioreactors:

on one hand, the bubbles mechanically stress the microalgae and may harm fragile microorganisms; and on the other hand, bubbles capture by surface-active effect the bodies which present the surfactant properties, in particular organic molecules, cellular debris and excretion products of living cells. These substances, usually dispersed in the medium in the absence of bubbles, are thereby assembled in the form of aggregates at the free surface of the head tank when the bubbles burst. Bacteria and fungi that could not develop due to the high dilution of these organic bodies find then concentrated substrates favorable to their development.

One of the purposes of the present invention is to avoid, or at least limit, the formation of bubbles in order to:

contain the bacterial and fungal development, for example to remain compatible with the health standards conventionally imposed in microorganism cultivation; and to limit the mechanical stresses in the liquid culture medium, and thus allow the cultivation of certain fragile microorganisms which were so far excluded from such a culture in reactor.

In an alternative embodiment of the airlift, the deoxygenation of the liquid culture medium flowing in the photobioreactor is achieved by gravitationally dropping the liquid medium in a container to a constant level. The liquid culture medium here is put into circulation by a pumping means, in particular of the centrifugal pump type, disposed in the reaction pipe designed not only to compensate for head losses in the pipe but also to elevate the cultivation of the drop height.

Although it generates fewer bubbles, this device with centrifugal pump is at least as mechanically damaging to microorganisms as the airlift. Indeed, in order to overcome the head losses, there is a generation, at each passage through the pumping means, of mechanical stresses that can hinder the growth of microorganisms and cause mortalities within the culture. The production performances become thus altered, sometimes in an unacceptable manner.

Generally, the shears create tensions that can alter cellular integrity by tearing of the wall of microorganisms and effusion of the cytosol, and the accelerations alter the structure of the cell by an increase in the gravitational field.

In addition, the Applicant has observed that the yield in the culture of photobioreactors equipped with airlifts or centrifugal pump was limited in particular because of mechanical stress imposed on photosynthetic organisms. Indeed, the Applicant has established that these stresses arise largely from the phenomena involved in the gas-liquid transfer in order to improve its efficiency and to avoid the inhibitory effects of high oxygen content. Modeling the gas-liquid transfer of carbon dioxide intended to the reaction and the oxygen that it produces requires the determination of the transfer speed that is characterized by the surface transfer coefficient.

This surface transfer coefficient is equal to the product of the volumetric coefficient of matter transfer to the liquid "$K_L$" ($m \cdot s^{-1}$) and the interfacial area related to the volume "a" ($m^{-1}$), and therefore depends on the geometry of the gas/liquid exchange system but also on the physicochemical properties of the liquid and gas. In the case of a gas/liquid exchange within a vertical bubble column, the exchange surface depends on the number of bubbles and on their size. The population of bubbles generated by injection of gas in a liquid depends on the injection flow rate, on the geometry of the injector, and on the pressure difference on either side thereof.

BRIEF SUMMARY

The present invention aims, in particular, to provide a photosynthetic reactor which allows mass cultivation of photosynthetic microorganisms, and its extension to the most fragile species, with a reactor that meets the following issues:

reducing, even avoiding, the mechanical stresses which are generally related to the stirring and circulation of the culture medium and which decrease the survival and growth performances of photosynthetic microorganisms such as microalgae, and in particular, chain-form microalgae provided with appendices;

reducing, even preventing, the production of small size bubbles likely to promote aggregation of organic molecules and development of heterotrophic microorganisms to whom they serve as a substrate;

while performing the photon transfer, to deliver the solar radiation to photosynthetic microorganisms, the mass transfer or gas/liquid transfer indispensable in conveying carbon and evacuating oxygen, and the heat transfer, to evacuate the calories conveyed by radiation and maintain the culture at the right temperature; and while maintaining mechanical conditions that preserve the integrity of cells and avoid the exchanges with the surrounding environment likely to lend itself to contamination and dissemination.

Regarding closed photosynthetic reactors described hereinabove, their biggest limitation to the development of algae production comes from the fact that they are intended to the planet's surface area, which are used, as a priority, for urbanization and food crops for food purposes, and have a scarcity steadily climbing with human demography. This lack of surface area severely limits the development by these microalgae cultivation means, in particular, for energy purposes, which, in order to play a significant role, must occupy considerable surface areas.

Yet, the bodies of water, such as natural and artificial lakes of continents, and especially seas, cover the largest surface areas on Earth and are still poorly showcased for their exposure to light.

The invention proposes a reaction casing for a photosynthetic reactor suitable for cultivating photosynthetic microorganisms, which can be spread over the surface of lakes and seas. For this purpose, the invention proposes to use these water bodies receiving solar radiation to ensure, apart from the water resource, two essential functions of photobioreactors, namely the horizontal surface lift and thermal stability.

Several types of photosynthetic reactors spread over a water body are known from the state of the art, so that to answer this problematic use of water bodies.

It is thus well known, from the patent application FR 2 621 323, to provide a photobioreactor including a reaction casing made in the form of a first set of parallel tubes, from flexible plastic material, such as polyethylene, connected together at their two ends by two collectors upstream and downstream respectively. This first set of tubes ensures containment of the liquid culture medium. The photobioreactor further comprises a second set of tubes placed under the first set of tubes, where the tubes of this second set are intended to be inflated with compressed air to form a pneumatic floating support. Such a photobioreactor presents many drawbacks, the main ones being: a complex and costly reaction casing with a succession of tubes and of upstream and downstream collectors that weigh down the reaction casing and a complex structure intended to ensure flotation of the reaction casing on the imposed water body in particular by the presence of these collectors.

The documents FR 2 361 060 and FR 2 324 224 respectively describe a photosynthetic reactor including a reaction casing made in the form of a series of transparent tubes connected together to delimit a path of continuous flow, with a coil shape, for the liquid culture medium. These tubes are housed in a frame to form a floating structure including flotation containers. Such a reactor has many drawbacks, the main ones being: a complex and costly reaction casing with a succession of tubes connected together at their ends, these tubes requiring a complex structure intended to ensure the flotation of the whole.

The document WO 2009/051479 A2 describes a photobioreactor including a reaction casing made in the form of a series of transparent tubes connected together by coupling pieces to delimit a continuous flow path, with a coil shape, for the liquid culture medium. To ensure flotation of these tubes, the photobioreactor comprises floats attached on the tubes. Such a photobioreactor presents many drawbacks, the main ones being: a complex and costly reaction casing with a succession of tubes connected together at their ends by coupling pieces, these tubes requiring the addition of floats intended to ensure flotation of the whole.

The document WO 2008/134010 A2 describes a photobioreactor provided with a reaction casing made in the form of a tube from flexible and transparent material performing the containment of liquid and gas volumes, and floats disposed on the sides of the tube to ensure flotation of the whole. The deployment of the containment volume is obtained by means of stiffeners and spacers and the two-phase gas/liquid circulation is done in one direction. In this photobioreactor, the tube must be connected at its both ends to other installations ensuring the moving and the closing of the loop of the reaction liquid.

The document WO 2009/090549 A2 describes a photobioreactor provided with a reaction casing made in the form of a tubular pocket from flexible and transparent material. In this photobioreactor, the gas supply ($CO_2$) to the liquid culture medium can be achieved by passive diffusion of gas over a wide area of the liquid medium, by injection of gas bubbles, in particular in the bottom portion of the reaction pocket, all of the aforementioned drawbacks being related to the production of bubbles.

The reactors described in the aforementioned documents FR 2 621 323, FR 2 361 060, FR 2 324 224, WO 2009/051479 A2, WO 2008/134010 A2 and WO 2009/090549 A2, also have a common additional drawback: cleaning of the reaction casing, from the inside and the outside, is particularly complex and requires a disassembly, at least partial, of the casing, knowing that the growth of fouling or of biofilms on the internal or external walls of the reaction casing hinders the transparency of the reaction casing and therefore the production yield of the photosynthetic organisms.

In order to overcome all or part of the drawbacks and issues raised hereinabove, the present invention proposes for this purpose a reaction casing for a photosynthetic reactor suitable for cultivating photosynthetic microorganisms, in particular algae, said reaction casing being designed, on one hand, to float on an expanse of water, on the other hand, to delimit a two-phase flow pathway for a gas/liquid culture medium between a first and second openings of said reaction casing, said reaction casing being remarkable in that it comprises, on one hand, an upper membrane and a lower membrane made at least partially of a flexible material, hermetically sealed and transparent to light radiation, said membranes being hermetically connected to each other by junction lines delimiting adjacent inflatable cells and, on the other hand, junction elbows joining pairwise said cells so that to define said generally sinuous-shaped flow path, one of the cells being in fluid connection with the first opening and another cell being in fluid connection with the second opening.

With this casing, the two-phase flow pathway has an overall sinuous or serpentine shape, and takes place, between the first opening and the second opening, in the succession of cells and junction elbows; the length of said path being primarily dependent on the length of the cells, junction elbows being essentially used to assign the path this sinuous shape in order to limit the final length of the casing.

Hence, this casing allows the production of photosynthetic microorganisms, in particular microalgae, by monoclonal culture in controlled conditions, that can be spread over the surface of a water body (lake or sea). This casing should contribute to the showcasing of these water bodies which have the most abundant and the least showcased planet's areas, for the production of the photosynthetic microorganisms.

Indeed, the casing is proposed to exploit several intrinsic characteristics of water bodies, namely:
thermal inertia bound to the significant heat capacity of water which, by the exchange with the culture medium through the outer sheath, allows to keep the temperature at levels close to the optimum of the cultured photosynthetic microorganisms,
the ability to lift bodies having a density lower than that of water, which allows to ensure the hydrostatic retention of culture volume on the surface according to the natural horizontality of lakes, avoiding thereby gravitational flows and formation of undesirable bubbles; and
the transparency of water bodies, when they don't receive silty feed.

The water body may serve as a local source of water for the culture, but it is desirable to treat it in order to remove unwanted microorganisms, and certain substances such as excess minerals.

The present casing applies to the cultivation of any photosynthetic organism, that is to say all life-forms capable of development by means of photosynthesis in a nutritive and appropriate culture medium, in the presence of solar radiation and carbon, in particular in the form of carbon dioxide.

This reaction casing, suitable for water bodies, allows executing the following functions:
ensuring containment time of the culture by preventing the exchanges of matter with the surrounding environment that lend themselves to contamination and dissemination, and, for that reason, withstanding the mechanical stresses in particular currents, winds, and surface agitation;
ensuring the photon transfer in order to deliver solar radiation to the microorganisms in culture;
ensure the indispensable gas/liquid mass transfer in order to provide carbon and evacuate oxygen from the reaction;
ensuring the heat transfer, in order to evacuate the calories provided by radiation and maintain the culture at the right temperature;
becoming suitable for reduction of the production costs of the produced biomass by a moderate cost of the implemented means in this casing.

The casing according to the invention allows to obtain these results, and presents for this a particular containment, with successions of cells connected together by junction elbows and thus delimiting a single path of continuous flow of liquid and gas reaction media, which lend itself to the scaling-up towards large surfaces; the crop production of the photosynthetic microorganism production systems being, in fact, proportional to this surface by a factor called surface productivity, value of which is in the order of tens of grams of dry matter per square meter and per day.

Both membranes are made from a flexible material suitable for allowing inflation, but also for allowing bending, transverse deformation and/or flexion of the casing; each membrane being made from a sheet or film, or even an assembly of sheets or films.

It is understood by flexible material a material that can be deformed, bent, rolled, and flexed without cracking or breaking, such as a flexible or ductile material. Such material is particularly suitable for the casing according to the invention because it allows that:

- the casing can be folded or rolled in whole or part in order to be stored in a folded or rolled form, before being spread over the water body by inflation, such inflation being carried out by filling by way of gas and/or liquid before establishing their back-and-forth circulation;
- the casing membranes deform and flex in order not to break under the effect of wind and water body movements;
- the manufacturing costs of these casings are reduced with the use of a relatively economic flexible material.

Using a flexible or expandable material is to be preferred to lend itself to deformations at the ends of the casing.

According to one characteristic, the cells comprise a plurality of cell pairs, each cell pair comprising:

- a cell called departure cell defining a circulation of the liquid culture medium from an upstream portion of the casing to a downstream portion of the casing, where one of the departure cells is in fluid connection with the first opening disposed in the upstream portion of the casing; and
- a cell called return cell defining a circulation of liquid culture medium from said downstream portion to said upstream portion, where one of the return cells is in fluid connection with the second opening disposed in the upstream portion of the casing;

and junction elbows alternately comprise downstream junction elbows disposed in the downstream portion of the casing and upstream junction elbows disposed in the upstream portion of the casing in order to connect pairwise departure and return cells.

This geometrical characteristic is advantageous so as to limit the longitudinal overall-dimension of the casing, while increasing the length of the two-phase flow path; the length of said two-phase flow path substantially corresponding to the sum of the lengths of the cells.

In an advantageous manner, the junction elbows are of the inflatable type and are made at least partially from a flexible and hermetically sealed material.

According to another characteristic, each cell is delimited by two rectilinear junction lines to define a rectilinear portion of the flow path, and each junction elbow is delimited at least externally by a junction line, substantially bent by 180° and having two ends connected to two rectilinear junction lines delimiting two adjacent cells.

Thus, the cells are substantially rectilinear and parallel with each other with elbows by 180°.

In one particular embodiment, the ends of each bent junction line and/or the free ends of the rectilinear junction lines located inside the corresponding junction elbows are provided with reinforcement means, in particular the eyelet, rivet or bolt type hermetically passing through the two membranes.

Indeed, concentrations of tension occur due to inflation of the casing, in particular at the free ends of the rectilinear junction lines separating two communicating cells and at the ends of bent junction lines. These ends can thus become advantageously reinforced by reinforcing means of the eyelet, rivet or bolt type passing through the membranes, in the manner of padding punctures. These reinforcing means are preferably designed to strongly apply the membranes one against the other so that their assembly remains hermetically sealed despite their piercing.

Advantageously, each bent junction line has either an overall semicircle shape, or an overall broken line shape made up of several rectilinear segments.

The advantage of these shapes is to ensure a turn for the flow path between two cells, while meeting the constraints imposed by the inflation of the casing.

According to a first embodiment of the inflatable junction elbows, the casing is made from only the upper and lower membranes, said membranes being hermetically connected together according to the junction lines alternately delimiting the inflatable cells and the inflatable junction elbows.

Therefore, the casing is composed of a single piece resulting from the assembly of the two membranes.

According to a second embodiment of the inflatable junction elbows, the casing is composed of three distinct portions, namely an upstream portion, a downstream portion and a central portion sandwiched between the upstream and downstream portions, where:

- the upstream portion is composed of an assembly of an upper skin and a lower skin hermetically connected together according to the junction lines to delimit both upstream portions of cells and upstream junction elbows, the two openings being provided in this upstream portion;
- the downstream portion is composed of an assembly of an upper skin and a lower skin hermetically connected together according to the junction lines to delimit both downstream portions of cells and downstream junction elbows; and
- the central portion is composed of an assembly of an upper skin and a lower skin hermetically connected together according to the junction lines to delimit only the central portions of the cells.

In a variant of inflatable elbows, the junction elbows are of the rigid type and are attached to the ends of the inflatable cells.

In one particular embodiment, the cells define rectilinear portions of the flow path which are parallel to a longitudinal direction of the casing and which have substantially equivalent lengths.

According to one possibility of the invention, the junction lines are of the welding, sewing, gluing or clipping line type between the two membranes.

The present invention also relates to a photosynthetic reactor suitable for cultivating photosynthetic microorganisms, in particular algae, including:

- at least one reaction casing according to the invention;
- at least one closing pipe ensuring the fluid connection between the first and second openings of said reaction casing;
- at least one circulation means disposed in said closing pipe and designed to put into circulation the liquid culture medium in the closing pipe and the reaction casing;
- at least one liquid injection means disposed in said closing pipe and designed to allow liquid to be injected into the reaction casing;
- at least one gas injection means disposed in said closing pipe and designed to allow gas to be injected into the reaction casing;
- at least one liquid outlet means for harvesting the photosynthetic microorganism culture; and
- at least one gas exhaust means disposed in said closing pipe and designed to allow the escape of gas injected into the reaction casing.

This reactor can of course include several reaction casings with a circulation means common to all these casings; the or each casing defining a unique pipe from and up to the closing pipe which ensures the connection between the two openings of the casing forming the inlet and the outlet.

With a reactor according to the invention, the liquid culture medium and the gas flow simultaneously in contact with one another along the substantially horizontal two-phase flow path because the reaction casing, and therefore the cells and junction elbows delimiting this path, float on the water surface which is mainly horizontal (to the variations induced by wind, waves, surface movements, etc.), and exchange some components along their common path. The exchanges between the liquid culture medium and the gas are proportional to the length of the cells, which allows to consider large scale increases.

The reactor and the reaction casing according to the invention are thus specially designed to increase the efficiency for gas-liquid transfer and to decrease the mechanical stresses inflicted to the organisms in culture in order to extend production to fragile species.

In addition, the reactor and the reaction casing according to the invention allow to limit the formation of small diameter bubbles and thus to reduce the development of heterotrophic microorganisms consuming oxygen. Indeed, with the reaction casing according to the invention, the gas/liquid transfer is no longer done inside a vertical bubble column but along a substantially horizontal flow path in which the flow follows a regime of the horizontal two-phase type, in particular of the stratified flow type or of the pockets flow type or of the elongated bubbles type.

Contrary to the aforementioned principle according to which the reaction takes place only in the liquid phase, the Applicant has assumed that the gas is an integral part of the reaction and must be admitted into the reaction volume in the same way as the liquid. In privileging horizontal two-phase flow regimes (stratified, with pockets or with elongated bubbles), the exchange surface between the gas and the liquid is extended to the entire path in the reaction casing with bubble production clearly less abundant than in the case of some reactors of the prior art, thereby reducing the observed deleterious effect of these bubbles.

In addition, in the reactor according to the invention, the circulation of the liquid culture medium is ensured by one or more circulation means generating reduced shear and centrifugal forces.

Advantageously, the closing pipe has an overall "U" or "V" shape and comprises:
an ascending portion provided with an upper portion in fluid connection with the first opening; and
a descending portion provided with an upper portion in fluid connection with the second opening;
the descending portion and ascending portion being provided with respective lower portions in fluid connection, and circulation means being designed to put in circulation the liquid culture medium in the reaction casing from the first opening to the second opening.

Thus, the overall "U" or "V" shape of the closing pipe, with a descending portion (otherwise called plunging upstream branch) and an ascending portion (otherwise called rising downstream branch), is intended to block the gas at the upstream (in other words at the outlet of the casing which corresponds to the second opening), in order to avoid its recycling and also so that the gas does not reduce the performances of the circulation of the liquid.

In a first particular embodiment, the injection liquid means is disposed in the upper part of the ascending portion, and the gas injection means is disposed in the ascending portion, at the top part or the bottom part of said ascending portion, and furthermore:
either the gas exhaust means and the liquid outlet means are composed of a common duct disposed in the upper part of the descending portion, said common duct being provided with a free end fixed to an adjustable height with respect to the water body;
or the gas exhaust means is composed of a first output duct disposed in the upper part of the descending portion, the outlet port towards said first output duct being optionally provided with a closure with float, and the liquid outlet means is composed of a second outlet duct disposed in the lower part of the one or other of the descending and ascending portions and provided with a free end fixed to an adjustable height with respect to the water body.

In this first embodiment, a co-current flow is implemented with the liquid and gas entering the casing through the first opening and leaving the casing through the second opening, so that the liquid and gas flow through the casing in the same direction; the injection of liquid being carried out downstream of the circulation means, at the inlet of the casing which corresponds to the first opening.

When the gas exhaust means and liquid outlet means are composed of a common duct, the free end of this common duct forms a high point that will establish an overpressure of the inflation inside the casing in order to stretch the membranes; such inflation overpressure avoiding that folds do not form due to lack of tension in the membranes of the casing, which would lead to a decrease in volume of fluids that could cause surges by free surface and other water-hammers in the case of the agitation of the water body, which would cause sudden tensions that can tear up the membranes.

When the gas exhaust means and the liquid outlet means are composed of two distinct outlet ducts, the free end of the second outlet duct of the liquid form a high point that will establish an overpressure of the inflation in the casing in order to stretch the membranes and avoid folds. The presence of a closure with float at the outlet port of the first gas outlet duct is advantageous to avoid liquid exits.

In a second particular embodiment, the liquid injection means is disposed in the upper part of the ascending portion, and the gas injection means is disposed in the descending portion, preferably in the upper part of said descending portion, and besides, gas exhaust means comprises a first outlet duct disposed in the upper part of the ascending portion and the liquid outlet means comprises a second outlet duct disposed either in the upper part of the descending portion, or in the lower part of either one of the descending and ascending portions, said second outlet duct being provided with a free end fixed to an adjustable height with respect to a water body.

In this second embodiment, a counter-current circulation is implemented with the liquid entering the casing by the first opening and leaving the casing through the second opening and with the gas entering the casing through the second opening and leaving the casing through the first opening, so that the liquid and gas flow through the casing in opposite directions of circulation; the injection of liquid being carried out at the inlet of the casing, downstream of the circulation means.

According to a first possibility of the invention, the circulation means comprises a gas lift device and comprises a gas injection duct disposed in the lower part of the ascending portion, said gas injection duct also constituting the gas injection means; the implementation of this gas lift device being possible only with a co-current circulation.

This gas lift device allows to avoid use of mechanical systems likely to cause shearing for microorganisms.

However, the gas flow rate related to the circulation is not always corresponding to the one necessary to the gas-liquid exchanges, which may result in erratic operations.

According to a second possibility of the invention, the circulation means comprises a circulation mechanical device, in particular of the motor-rotationally driven propeller type or of the centrifugal pump type, said circulation mechanical device being disposed in the ascending portion.

In order to separate the circulation function from that of the gas injection for exchanges of gas-liquid mass, and thus to control the gas flow rate necessary for these exchanges, it is advantageous to use a circulation mechanical device, which preferably allows the passage of cleaning bodies flowing in the reactor.

In the case of a co-current circulation with this mechanical device, the gas injection means comprises a gas injection duct disposed in the upper part of the ascending portion.

The invention also relates to a method for cultivating photosynthetic microorganisms, in particular algae, using a reactor according to the invention comprising the following steps:
  injecting a liquid culture medium in the reaction casing according to a flow rate control with the liquid injection means;
  injecting gas into the reaction casing according to a flow rate control with the gas injection means;
  circulating the liquid culture medium with the circulation means;
  controlling the circulation means and gas injection means in order to establish in the reaction casing a regime for gas/liquid culture medium to flow in two-phases, in particular of the stratified flow type or of the pockets flow type or of the elongated bubbles type.

According to one characteristic, the control step comprises a step of controlling the circulation speed of liquid in the reaction casing between approximately 0.1 and 1.0 m/s, and a step of controlling the circulation speed of gas in the reaction casing between approximately 0.5 and 2.0 m/s.

This characteristic is advantageous to avoid the appearance of decanting zones and other zones of acceleration likely to create undesirable heterogeneities along the path.

According to another characteristic, the circulation means comprises a motor-rotationally driven propeller, and the speed of propeller rotation is less than approximately 1000 rpm, preferably less than approximately 100 rpm.

According to one characteristic, the injection of the liquid culture medium and of gas in the reaction casing is performed in order to inflate and spread the casing over the surface of water body.

The invention also relates to a method for manufacturing a reaction casing according to the invention, comprising the following steps:
  providing an upper membrane and a lower membrane at least partially made from a flexible material, hermetically sealed and transparent to light radiation;
  hermetically connecting said membranes according to junction lines delimiting the inflatable cells; and
  providing elbow junctions joining pairwise said cells to define a flow path with overall sinuous shape between a first opening and a second opening provided in said casing.

BRIEF DESCRIPTION OF THE DRAWINGS

Other characteristics and advantages of the present invention will appear after reading the detailed description hereinafter, the several non-limiting examples of embodiments, made with reference to the drawings in which:

FIGS. 4a and 4b are schematic top views of two embodiments of the junction elbow for a casing according to the invention;

FIGS. 5a to 5c are schematic cross-sectional top and side views, respectively, of a first reactor according to the invention using as circulation means a gas lift device;

FIGS. 14a and 14b are schematic top views of a reaction casing according to the invention, according to a third assembly mode, respectively before and after assembly.

DETAILED DESCRIPTION

Figure 1:
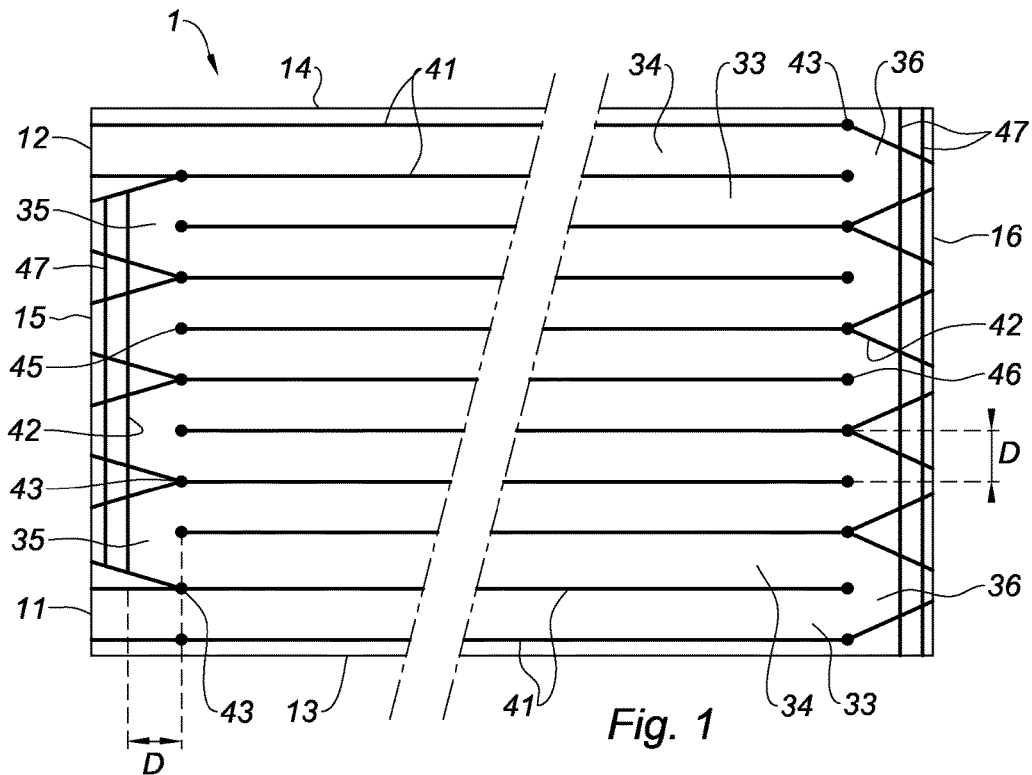
FIG. 1 is a schematic top view of a reaction casing according to the invention, according to a first assembly mode, with a flow path composed of five back-and-forth paths.

The description of a reaction casing 1 according to the invention, according to a first assembly mode, for a photosynthetic reactor 2 or photobioreactor, is made with reference to the FIGS. 1 to 4; this casing 1 is suitable for cultivating photosynthetic microorganisms, in particular algae, and in particular for cultivating photosynthetic microorganisms sensitive to mechanical stresses.

The casing 1 is designed, on one hand, to float on a water body and, on the other hand, to delimit a path for a gas/liquid culture medium to flow in two phases between a first opening 11 and a second opening 12 of the casing 1.

This inflatable casing 1, with an elongated shape along a main longitudinal axis, is made by assembly of an upper membrane 31 and a lower membrane 32 made from a flexible material, hermetically sealed and transparent to light radiation. The casing 1 has two opposite longitudinal edges 13, 14 extending along the main longitudinal axis, and two opposite lateral edges, respectively, upstream lateral edge 15 and downstream lateral edge 16, extending along a secondary lateral axis; the upstream lateral edge 15 being hence disposed in a portion called upstream of the casing 1 while the downstream lateral edge 16 is disposed in an opposite portion called downstream. The two openings 11, 12 are arranged on the upstream lateral edge 15, and thus in said upstream portion, and spaced apart from one another, with the first opening 11 arranged in the vicinity of a longitudinal edge 13 while the second opening 12 is arranged in the vicinity of the other longitudinal edge 14.

These membranes 31, 32 are substantially equivalent in size and shape, and have in particular an overall rectangular shape with a longitudinal dimension (or length) greater than the lateral dimension (or width). The membranes 31, 32 have in particular a length of several tens of meters long, for example in the order of 50 meters.

The membranes 31, 32 are hermetically connected to each other according to junction lines 41, 42 delimiting alternately:
inflatable cells 33, 34; and
inflatable junction elbows 35, 36 joining pairwise the cells 33, 34 in order to define a unique flow path with an overall sinuous shape.

In this way, the cells 33, 34 which extend along the main longitudinal axis, in other words in the direction along the membranes 31, 32, are connected end-to-end or communicate together by junction elbows 35, 36 to form together a single coil-shaped pipe.

Figure 2:
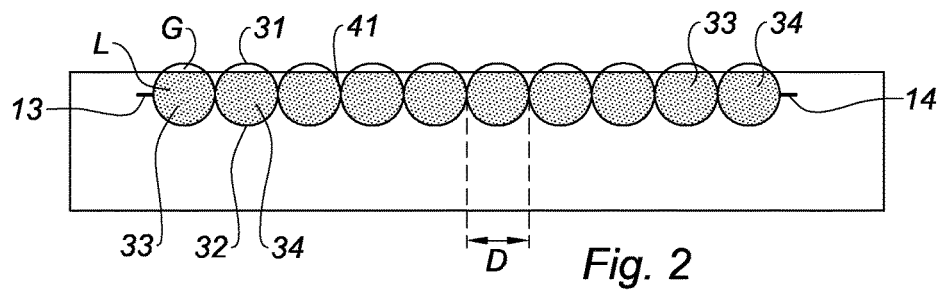
FIG. 2 is a schematic cross-sectional view of the casing of FIG. 1 after inflation.
Figure 3:
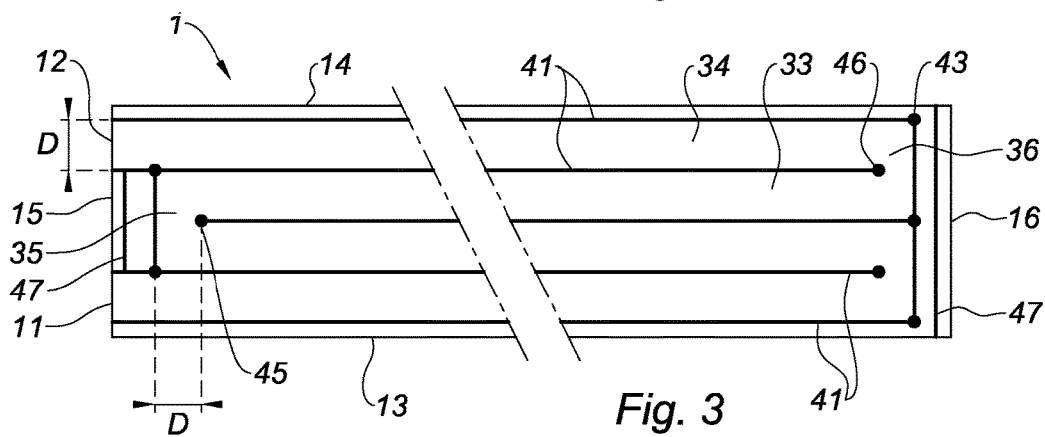
FIG. 3 is a schematic view of the reaction casing according to the invention, according to a first assembly mode, with a flow path composed of two back-and-forth paths.

The cells 33, 34 comprise a plurality of pairs of cells, for example, five pairs of cells in the example of FIGS. 1 and 2 or two pairs of cells in the example of FIG. 3, each pair of cells comprising:
cell called departure cell 33 defining a circulation of the liquid culture medium from the upstream lateral edge 15 to the downstream lateral edge 16 of the casing 1, where the first departure cell 33 of the sinuous flow path is in fluid connection with the first opening 11; and
a cell called return cell 34 defining a circulation of the liquid culture medium from the upstream lateral edge 16 to the downstream lateral edge 15, where the last return cell 34 of the sinuous flow path is in fluid connection with the second opening 12.

Thus, the number of cells 33, 34 is even such that the first opening 11 (inlet of the liquid medium in the casing 1) and the second opening 12 (outlet of the liquid medium in the casing 1) are on the same upstream lateral edge 15. The upstream lateral edge 15 is thus provided with the two openings 11, 12, with eventually a lateral junction line 47 extending between the two openings 11, 12, while the downstream lateral edge 16 is hermetically closed by at least one lateral junction line 47 in addition to the junction lines 42.

The junction elbows 35, 36 alternately comprise:
downstream junction elbows 36 disposed in downstream portion of the casing 1 and joining by 180° a departure cell 33 and a return cell 34 of a same pair of cells 33, 34; and
upstream junction elbows 35 disposed in upstream portion of the casing 1 and joining by 180° a return cell 34 and a departure cell 33 of two adjacent pairs of cells 33, 34.

Thus, the sinuous flow path is delimited successively, from the first opening 11 to the second opening 12, through the first departure cell 33, the first downstream junction elbow 36, the first return cell 34, the first upstream junction elbow 35, the second departure cell 33, and so on until the last downstream junction elbow 36 and finally the last return cell 34.

Each cell 33, 34 is delimited by two rectilinear junction lines 41 to define a rectilinear portion of the rectilinear flow path, and thus the cells 33, 34 define the rectilinear portions of the flow path which are parallel to the main longitudinal axis of the casing 1 and which have substantially equivalent lengths.

The length of a casing 1 depends on the lake and on fluid supplies. With the number of cells 33, 34, this length will determine the productivity of the reactor. For example, based on an average productivity of 10 g/m$^2$/day, a casing of 50 m long with four cells operating eight months a year should be able to produce 80 kg of dry matter per year.

As shown in FIGS. 1, 3 and 4, each elbow junction 35, 36 is delimited:
externally by a junction line 42 substantially bent at 180°, each bent junction line 42 having two ends 43 connected to two rectilinear junction lines 41 delimiting two adjacent cells 33, 34; and
internally by a free end 45, 46 of the rectilinear junction line 41 concerned, in other words an upstream end 45 for an upstream junction elbow 35 and a downstream end 46 for a downstream junction elbow 36.

Once inflated, and as shown in FIG. 2, the cells 33, 34 of the casing 1 have an overall tubular shape with a circular section of diameter D.

FIGS. 4a and 4b illustrate:
in dashed lines, the junction lines 41, 42 after inflation, with rectilinear junction lines 41 spaced apart from one another by a distance corresponding to the aforementioned diameter D; and
in continuous lines, junction lines 41, 42 after inflation, with rectilinear junction lines 41 spaced apart from one another by a distance equivalent to $\pi$ D/2 greater than D.

Therefore, between deflation and inflation, the rectilinear junction lines 41 approach a distance equivalent to D ($\pi/2-1$). Furthermore, the bent junction lines 42 make a 180° turn.

A difficulty in performing these turns, in other words these bent junction lines 42, is that these lines undergo, on one hand, a deformation between performing the lines 42 and the flat cuttings and, on the other hand, a tubular deformation they adopt during inflation, of folds resulting from narrowing of the junction lines 41, 42 during inflation.

An embodiment of the bent junction lines 42 is hence provided which limits the folds in order to reduce the concentrations of tension that could create zones of fragility on the membranes 31, 32, as well as to avoid zones of retention of the culture difficult to access for cleaning bodies where biomass could accumulate.

In a first embodiment shown in FIG. 4a, each bent junction line 42 has an overall shape of a semicircle, in other words curved junction lines.

In a second embodiment shown in FIGS. 1 and 4b, each bent line junction 42 has an overall shape of a broken line formed of several rectilinear segments, in other words a cut-off corner line. As shown in FIG. 4b, the turning curvature is obtained with seven cut-off corners, i.e. the bent junction lines 42 are made with five rectilinear segments. The end rectilinear segments are intended to avoid that two consecutive turns collide during inflation due to the approaching of the rectilinear junction lines 41. For this purpose, these end rectilinear segments each form an angle equal to or greater than A compared to the main longitudinal axis which is independent of the diameter D of the tubes and which has the value:

$$A=\text{Arctan}(1-2/\pi)=19.97°.$$

As for the central rectilinear segment, it is perpendicular to the main longitudinal axis and located at a distance at least equal to $\pi D/2$ from the free end 45, 46 of the concerned rectilinear junction line 41 at the deflated state. Two intermediate rectilinear segments join this rectilinear central segment to the respective end rectilinear segments to form cut-off corners or segments of adjacent lengths.

Similarly, in the embodiment of FIG. 4a, the distance between the free end 45, 46 and the peak of the semicircular bent junction line 42 is preferably greater than or equal to $\pi D/2$.

This minimum width of $\pi D/2$ for the junction elbows 35, 36 in their plane of symmetry is advantageous so that the distance between the floor and the ceiling, once the casing 1 is inflated, is sufficient to pass the cleaning bodies.

This second embodiment does not completely avoid the formation of folds but it reduces it; such folds resulting from the inevitable approaching of the rectilinear junction lines 41, but the elasticity of the material used for the membranes 31, 32 allows to limit them.

In a third embodiment shown in FIG. 3, the bent junction lines 42 are replaced by rectilinear junction lines orthogonal to rectilinear junction lines 41. However, although simple in design, such a conformation presents the drawback of forming culture retention zones in the corners with right angles, difficult to access by the cleaning bodies.

Other embodiments may be considered to limit the formation of folds, but this needs radial junction lines and cuts in the turns that substantially complicate the assembly of the membranes 31, 32.

It is to be noted that concentrations of tension can occur due to inflation, particularly at the ends of the junction lines 41, 42 separating two communicating cells 33, 34, that is to say, at the ends 43 of bent junction lines 42 and at the free ends 45, 46 of rectilinear junction lines 41 located inside the corresponding junction elbows 35, 36. These ends 43, 45, 46 are therefore advantageously reinforced by reinforcement means of the eyelet, rivet or bolt type passing through the membranes 31, 32, in the manner of padding punctures. These reinforcement means should strongly apply membranes 31, 32 against one another so that their assembly remains hermetically sealed despite their piercing.

Concerning the assembly of the two membranes 31, 32, the junction lines 41, 42 are of the welding, sewing, gluing or clipping type between the two membranes 31, 32. Thus, the back-and-forth path defined by the casing 1 is arranged by the junction lines 41, 42 by means of welds, seams, gluing or of clipping devices. Of course, other hermetic assembly techniques of flexible membranes can be considered, in particular the combination of the aforementioned techniques.

In the case of an assembly by heat sealing, it is possible to make the membranes 31, 32 pass in front of the heating devices equipping rotary machines. Generally, this assembly should preferably be done in a microbiologically controlled atmosphere so that casings can be presumed sterile at the end of manufacturing.

Regarding the packaging of a casing 1 in assembly outlet, it is possible to wind the casing 1 around an axis or floating mandrel F used for handling and ensuring the buoyancy of the casing 1 during its unwinding by inflation on the lake, as described hereinafter. The winding of the casing 1 is such that the downstream lateral edge 16 is located inside the winding, while the upstream lateral edge 15 is located in the periphery of the winding to ensure hermetic connection of the two openings 11, 12 with a closing pipe described subsequently. The winding of the casing 1 which therefore follows the assembly thus starts from only the downstream lateral edge 16 so that the upstream lateral edge 15 remains accessible for connection to the closing pipe. Once the casing 1 is unwound on the expanse of water, the downstream lateral edge 16 is free or eventually maintained while the upstream lateral edge 15 is hermetically connected with this closing pipe in order to complete the circuit.

The two membranes 31, 32 are made of a flexible material, in other words, a material suitable for folding, inflation, transverse deformation and/or deflection of the cells 33, 34.

Concerning the membranes 31, 32, the material should make it possible for them to resist:

the tension they are subjected to during inflation of the casing 1, and for this purpose, an overpressure which will be applied inside the casing 1 should not exceed a value to be set;

the tensile force related to displacement of the mass of the expanse of water, that of the air being negligible; and the return force of the mooring of the casing 1 onto a mooring support (floating craft E described hereinafter, at wharf or dock).

The Applicant has thus established a list of plastic materials used for the manufacture of membranes 31, 32, including in particular polyethylene, polypropylene, polyamides (nylon, Rilsan), polytetrafluoroethylenes (PTFE), either in the form of a membrane, in the form of woven fibers or in the form of composite fabrics, calendered or coated.

This list is obviously not limitative and may in particular, be supplemented with new transparent materials appearing on the market.

The multilayer co-extrusion can be used for example to make these membranes 31, 32 which are commonly used in agriculture. It is also advantageous to provide slightly extensible materials in order to allow for end deformations and limit the formation of creases.

FIGS. 5 to 7 illustrate photosynthetic reactors 2 according to the invention and adapted for the cultivation of photosynthetic microorganisms, in particular, algae.

Each reactor 2 includes:

at least one casing 1 in accordance with to the invention;

at least one closing pipe 5 ensuring the fluid connection between the first 11 and the second opening 12 of the casing 1, said openings 11, 12 being hermetically connected to said closing pipe 5;

at least one circulation means 6 disposed in the closing pipe 5 and designed for allowing the liquid culture medium L to circulate within the closing pipe 5 and within the casing 1;

at least one liquid injection means 71 disposed in the closing pipe 5 and designed to allow the injection of the liquid L in the casing 1;

at least one gas injection means 72 disposed in the closing pipe 5 and designed to allow the injection of the gas G in the casing 1;

at least one liquid outlet means 81 for harvesting the culture of photosynthetic microorganisms, such as a fluid;

at least one gas exhaust means 82 disposed in the closing pipe 5 and designed to allow the escape of the gas G injected into the casing 1.

The reactor 2 may comprise two distinct liquid injection means allowing injecting respectively the liquid culture medium and the inoculum in the reactor 2. These injection means may come in the form of injection ports allowing a connection to a source with asepsis control.

The reactor 2 may also comprise:

one or more sensors (not illustrated) disposed on the closing pipe 5 and suitable for providing the signals required for the control of the reaction, in particular, signals representing physical, chemical, or biological parameters of the quality of the culture, such as temperature, pH, rate of dissolved oxygen and turbidity of the liquid medium, etc. these controls are used in particular, to regulate injections of gas and liquid into the reactor 2;

means for controlling sterility (not illustrated) of gaseous and liquid media entering into and out from the space confined by the reactor 2, in particular some filters intended to prevent the access of contaminants;

regulation loops (not illustrated) interposed on the circuit of the culture and intended to regulate the main nutrient intakes of the culture, in particular, the admission of sterile medium by the concentration of dry matter, pH by the injection of $CO_2$.

The closing pipe 5 ensures closing the looping fluid path between the first 11 and the second openings 12 of the casing 1. The closing pipe 5 is made of a material that can be non-transparent to solar radiation and/or may be disposed away from light inside a closed area or a closed craft E as shown in particular, in FIGS. 9 to 11.

The closing pipe 5 exhibits a generally "U" or "V" shape and comprises:

an ascending portion 51 provided with a high portion or end 510 in fluid connection 30 with the first opening 11; and a descending portion 52 provided with a high portion or end 520 in fluid connection with the second opening 12.

The ascending portion 51 and the descending portion 52 are provided with respective low portions or ends 511, 512 in fluid connection. This general "U" or "V" shape of the closing pipe 5 is intended to block the gas upstream of the closing pipe 5, that is to say at the output of the casing 1 at the second opening 12, in order, on the hand, to avoid its recycling and, on the other hand, to prevent it from reducing the performance of the flowing of the liquid.

The ascending portion 51 and descending portion 52 are preferably tubular with an inner diameter substantially equivalent to the diameter D. The liquid injection means 71, such as a liquid pipe or liquid port, is disposed in the high portion 510 of the ascending portion 51, at the input of the casing 1 at the first opening 11.

In the embodiments of FIGS. 6 and 7, the gas injection means 72, such as a gas pipe or gas port, is disposed in the high portion 510 of the ascending portion 51, at input of the casing 1 at the first opening 11.

Figure 5B:
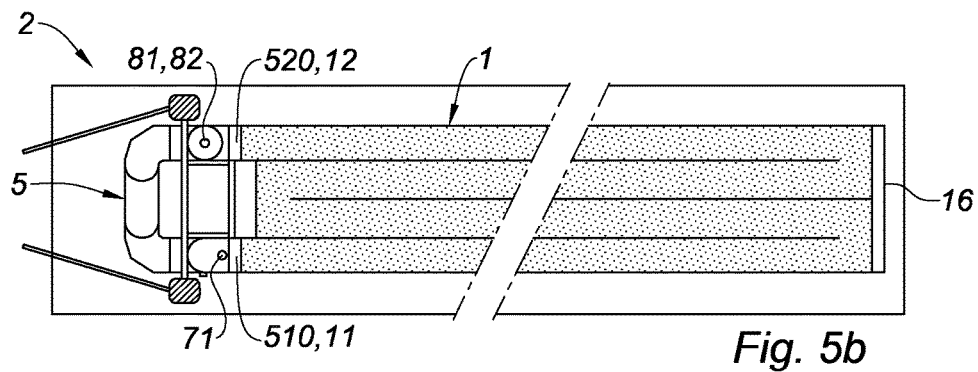
Figure 5C:
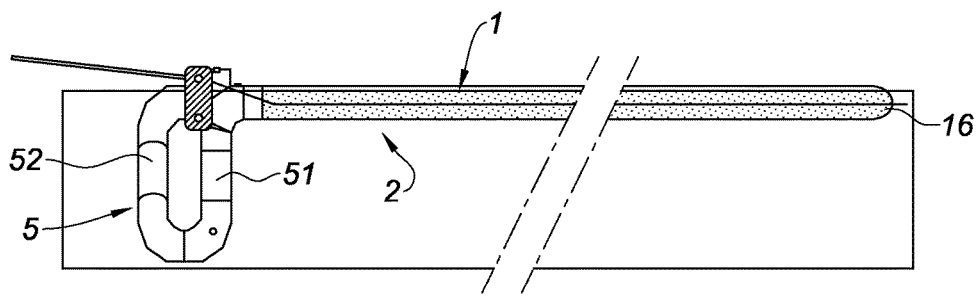
Figure 6A:
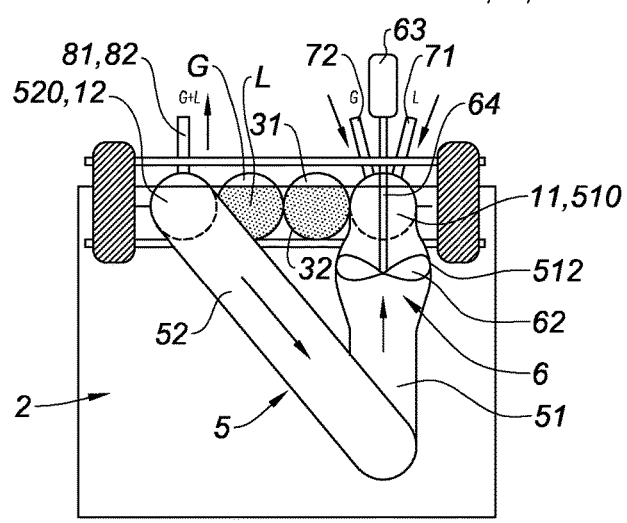
FIGS. 6a to 6c are schematic cross-sectional top and side views, respectively, of a second reactor according to the invention using as a circulation means a motor-rotationally driven propeller.
Figure 6B:
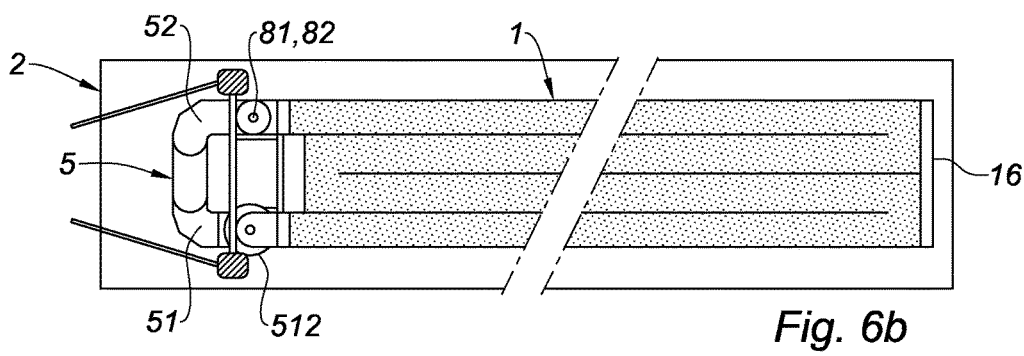
Figure 6C:
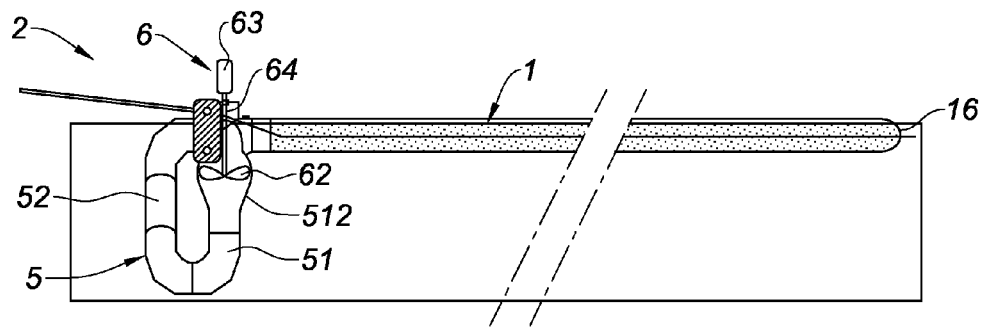
Figure 7A:
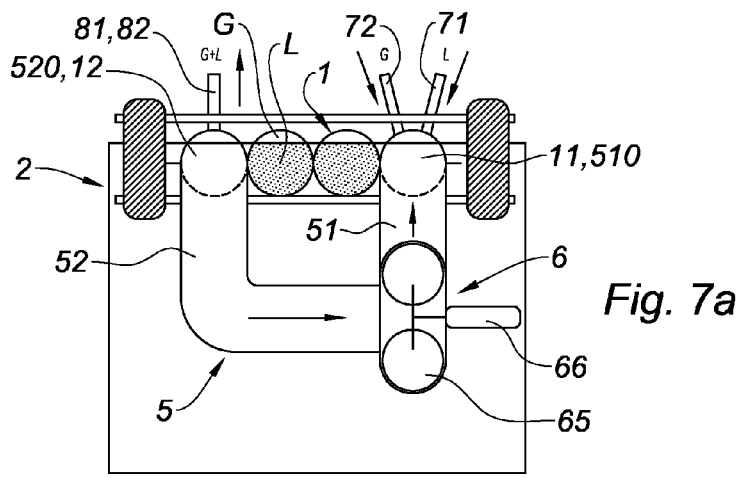
FIGS. 7a to 7c are schematic cross-sectional top and side views, respectively, of a third reactor according to the invention using as a circulation means a centrifugal pump.

In the embodiments of FIGS. 5 to 7, the gas exhaust means 82 and the liquid outlet means 81 are constituted of a common pipe 81, 82 disposed in the high portion 520 of the descending portion 52, this common pipe 81, 82 being provided with a free end set at an height adjustable with respect to the expanse of water; this height H, shown in FIGS. 6a and 7a, determining inflation overpressure of the casing 1 and able to be regulated in order to stabilize the inner flow depending on the agitation of the expanse of water. This height H is in the range of a few centimeters and can exceed several decimeters for casings of great length.

In this embodiment, the common pipe 81, 82 is placed in the high portion 520 of the descending portion 52, just before the descending portion 52 which plunges downwards, in order to evacuate the gas blocked in the descending portion 52.

In a non-illustrated embodiment, the gas exhaust means 82 comprises a first output pipe disposed in the high portion 520 of the descending portion 52, and the liquid outlet means 81 comprises a second output pipe disposed in the low portion 511, 521 of either one of the descending 51 and ascending 52 portions so as to only take the liquid L. The location in low portion of this second outlet pipe 81, where the culture is harvested, is chosen so as to minimize the influence of the injection of liquid media that would result in its dilution.

This second outlet pipe 81 is advantageously provided with a free end set at an adjustable height with respect to the expanse of water in order to establish the inflation overpressure. In this embodiment, the outlet orifice towards the first outlet pipe 82 is preferably provided with a closure with float intended to prevent the passage of liquid.

Thus, the output of the volume of surplus liquid L in the reactor 2 is carried out by this overflow comprising the common pipe 81, 82 in communication with the closing pipe 5. The point of communication of this common pipe 81, 82 with the closing pipe 5 is placed at the output of the casing 1, upstream of the sterile liquid injection means 71, as illustrated in FIGS. 5a, 6a and 7a, the arrows illustrating, in the figures, the flow direction of the liquid medium L. In fact, it is at the output of the casing 1 where the harvesting of the culture takes place and short circuits which would dilute it must be avoided.

This common pipe 81, 82, forming an overflow, constitutes a breakage of the containment of the liquid culture medium L. In order to avoid the retro-contamination of the culture in progress, the common pipe 81, 82 can usefully have a length of several meters, before opening into a harvesting tank, and be kept sterile by periodic cleaning.

As introduced hereinabove, the emergence of creases must be avoided, with an appreciable reduction of the reaction volume. In fact, such creases could cause surges and other hammerings in the case of agitation of the expanse of water, which would lead to brutal tension of the flexible material of the casing 1 liable to make it tear.

For this reason, the casing 1 must be continuously stretched using an inflation overpressure; a checking this overpressure should allow to maintain the casing 1 at a nominal level compatible with the agitation of the expanse of water and proper functioning of the assembly.

Thus, a method for cultivating photosynthetic microorganisms using such a casing 1 comprises a step of pressurizing the casing 1 consisting in creating an inflation overpressure within this casing 1.

The inflation overpressure of the casing 1 determines, as described hereinabove, its stiffness, in other words its resistance to deformation related to the agitation of the expanse of water, and the influence of the latter on the two-phase inner flow of the gas G and the liquid L; this overpressure being equal to the sum of the pressures of the gas and the liquid in the volume of the casing 1.

The control of the inflation overpressure also relates to detecting leaks. The output of surplus gas volume is carried out by gas exhaust means 82 described hereinabove and provided with an orifice set in high portion 520 of the descending portion 52. The gas is, for example, channeled to a filter that prevents the retro-contamination of the reactor before being released into the atmosphere or recycled. A control of the gas output rate may be carried out, by means of a means for controlling the gas flow rate, such as a needle valve, in order to adjust the height of the meniscus (liquid level or gas/liquid interface) in the casing 1.

In the embodiments described hereinabove and illustrated in FIGS. 5 to 7, a co-current circulation is implemented with the liquid and the gas entering the casing 1 through the first opening 11 1 via the second opening 12 in such a manner that the liquid and gas flow in the casing 1 in the same flow direction.

In non-illustrated embodiments, it is possible to provide a counter-current circulation which is implemented with the liquid entering the casing 1 through the first opening 11 and exiting the casing 1 through the second opening 12 and with the gas entering the casing 1 through the second opening 12 and exiting the casing 1 through the first opening 11, in such a manner that the liquid and gas flow in the casing in opposite flow directions. To this end, the liquid injection means 71 remains positioned at the input of the casing 1, in the high portion 510 of the ascending portion 51, while the gas injection means 72 is disposed at the output of the casing 1, in the descending portion 52 (high or low portion) so that the gas enters the casing 1 through the second opening 12. Furthermore, the liquid outlet means 81 remains positioned at the exit of the casing 1 (either in the high portion 520 of the descendant portion 52, or in low portion of the ascending portion 51 or the descending portion 52) still with a free end set at an adjustable height with respect to the expanse of water, whereas the gas exhaust means 82 is positioned at the input of the casing 1, in the high portion 510 of the ascending portion 51.

In general, the gas exhaust means 82 is designed for venting the gas or for recycling the gas through a filter to avoid the retro-contamination of the reactor 2. Preferably, the gas exhaust means 82 is fashioned in such a manner as to maintain the head loss through this filter as low as possible in order to control the pressure in the casing 1.

The circulation means 6 is designed for allowing the liquid culture medium L to circulate in the reaction casing of the first opening 11 towards the second opening 12, this liquid culture medium L thus flowing in the closing pipe 5, from the high portion 520 of the descending portion 52 to the high portion 510 of the ascending portion 51. Preferably, the circulation means 6 is chosen in such a manner as to generate reduced shearing and centrifugal forces. However, it is possible to use all types of pumping means and in particular, centrifugal pumps without departing from the scope of the invention.

In the first embodiment of the reactor 2 illustrated in FIGS. 5a to 5c, the circulation means 6 comprises a gas lift device and thus comprises a gas injection pipe 61 disposed in the low portion 511 of the ascending portion 51, this gas injection pipe 61 also constituting the gas injection means 72. In such a case, the circulation function is directly associated with that of the gas-liquid mass exchange; this gas lift device 6, of the gas siphon type ensuring both the pumping and the injection of gas.

In the two other embodiments illustrated in FIGS. 6 and 7, the circulation function is dissociated from that of the gas-liquid mass exchange which is ensured through their interface in the casing 1 and which is exerted on their entire length. Therefore, the circulation means 6 is constituted of a mechanical circulation device that is disposed in the ascending portion 51 of the closing pipe 5. In these embodiments, the gas injection means 72 comprises a gas injection pipe 72 disposed in the high portion 510 of the ascending portion 51, at the input of the casing 1.

In the second embodiment of the reactor 2 illustrated in FIGS. 6a to 6c, the mechanical circulation device 6 comprises a propeller 62 driven in rotation by a rotating motor 63 via an output shaft 64 of said motor 63. The motor 63 is disposed outside the reactor 2 and the output shaft 64 hermetically passes through the closing pipe 5 to open into a housing 512 provided in the ascending portion 51, this output shaft 64 bearing the propeller 62 which is thus, movable in rotation inside this housing 512.

Advantageously, the housing 512 of the propeller 62 is disposed between a divergence area and a convergence area of the closing pipe 5, in order to ensure hydraulic continuity without sudden variation of velocity, thus, in order to limit head losses, accelerations and the shearing forces undergone by the microorganisms.

According to an advantageous feature and as illustrated in FIGS. 6a and 6c, this housing 512 is disposed in a vertical portion of the ascending portion 51 and hence, the propeller 62 exhibits a vertical rotation axis, in order to allow the evacuation of gas G that may form in the housing 512 and thus avoid the cavitation phenomena.

Furthermore, and as shown in FIG. 6a, the disposition of the exhaust means 82 of the gas G upstream of the propeller 62, combined with the disposition of the propeller 62 the housing 512 upstream of the gas injection means 72 is also advantageous in order to prevent that the gas from flowing through the propeller 62 and impairing its operation.

Figure 7B:
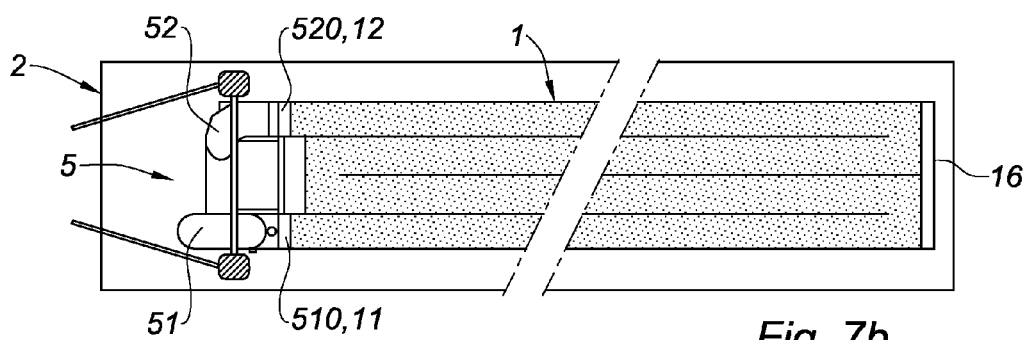
Figure 7C:
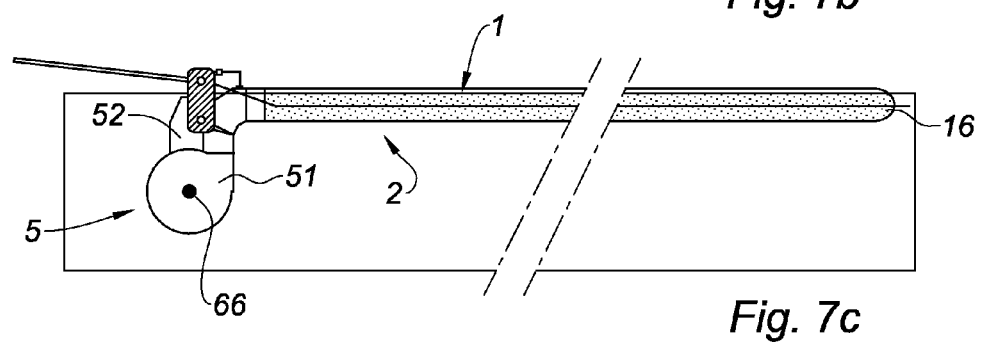

In the second embodiment of the reactor 2 illustrated in FIGS. 7a to 7c, the mechanical circulation device 6 comprises a centrifugal pump with a turbine 65 driven in rotation by a rotary motor 66; this turbine driving in rotation the mass of water axially entering in a volute of the closing pipe 5 in such a manner that it tangentially escapes under the action of the centrifugal force. The dimensions of the volute, the turbine blades as well as their number are selected to give room to the cleaning elements described below The reactor 2 may in fact include one or several cleaning elements (not illustrated) fashioned in such a manner as to circulate along the flow path, in other words inside the casing 1 and the closing pipe 5, in order to clean the inside of the casing 1 and closing pipe 5. In order to flow in a loop in the reactor 2, the cleaning element or elements are also fashioned in such a manner as to pass through the means 6 allowing the liquid culture medium to circulate, for example through the blades of the propeller 62 or through the turbine 65.

The cleaning element or elements, preferably spherical, exhibit for example a diameter lower than or substantially equal to the internal diameter D of the closing pipe 5 and the cells 33, 34 in order to optimize the cleaning of the internal walls of the closing pipe 7.

The difference in velocity between the gas flow and the liquid flow directly affects the gas/liquid mass transfers and must advantageously be maintained at the highest possible level. This is the reason why every cleaning element must not prevent the passage of gas. For this reason, each cleaning element is fashioned to let the gas pass at least partially inside the reactor 2 while being suitable for being driven by the circulation of the liquid culture medium so that the cleaning element does not affect the velocity difference between the gas and the liquid medium. To this end, the cleaning element or each cleaning element is made in the shape of a brush, in particular, spherical, comprising an assembly of hairs, bristles, strands or equivalent, with a central portion bearing these hairs. Thus, in the horizontal casing 1, the emerged hairs let the gas pass at the gas meniscus and the submerged central portion and the hair bearer exhibits a sufficiently large diameter for forming an obstacle to the passage of liquid such that the liquid medium draws the cleaning element with it.

In the same manner, the cleaning element can be achieved in the shape of a hollow sphere from elastomeric material. Advantageously, a substantial portion of the surface of the sphere can be pierced with holes which allow the gas to pass through. Certain cleaning elements may also present a density greater than that of the water in order to stay in contact with the floor of the casing 1 corresponding to its fully submerged lower or low portion.

The flexibility or elasticity of the cleaning elements further allow to reduce the culture retention areas which would result from the emergence of creases in the cells 33, 34 and/or the junction elbows 35, 36.

As shown in FIGS. 2, 5a, 6a and 7a, the circulation of the gas G and the liquid L, in counter-current or co-current, is done along a substantially rectilinear horizontal path where the gas G gathers in a volume located in the upper or high portions of the cells 33, 34 and the junction elbows 35, 36. Thus, an interface between the gas G and the liquid L is created which is the host of transfers related to the photosynthesis reaction. The longitudinal shape of this interface, and in particular, its continuous or discontinuous character, characterizes what is known as the state of flow. Without considering the influence of the agitation of the expanse of water, the states of flow in the casing 1 are substantially the same as in a horizontal pipe with a circular cross-section. These flows have been described under the names of stratified flow or slug flow or elongated bubbles flow.

Regarding the two-phase flows in horizontal pipes, certain works have indeed highlighted states of flow according to conditions of velocity, diameter, temperature, nature, pressure of circulating fluids, namely, in particular:
  dispersed bubbles flow, of Mandhane AD typology; and
  elongated bubbles flow, of Mandhane I typology;
  stratified flow and wavy stratified flow and smooth stratified flow, of Mandhane SS and SW typology;
  slug flow, of Mandhane I typology;
  annularmist flow, of Mandhane AD typology.

In the case of the present invention, the privileged states of flow are hence, located at the SS/I transition in the Mandhane typology, that is to say, between the stratified state and the slug state or elongated bubble state.

In the stratified regime, the gas/liquid interface comprises the free surface, the width of which varies with the level of liquid in the casing 1. In the slug or elongated bubbles state, the gas/liquid interface comprises the floor and ceiling of the slug or the elongated bubble. The mass transfers being proportional to the length of the path, the effect thereof on the performance of the reaction are reduced, which allowing considering large scale increases. The casings 1 can thus exhibit lengths of several hundred meters.

Figure 9A:
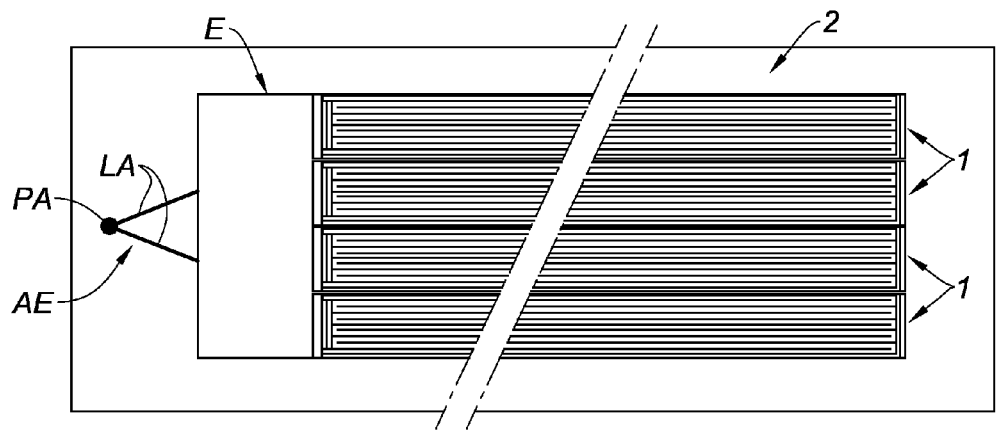
FIGS. 9a and 9b are schematic top and side views, respectively, of a reactor according to the invention including several casings secured only on one side of a floating craft.
Figure 9B:
Figure 9C:
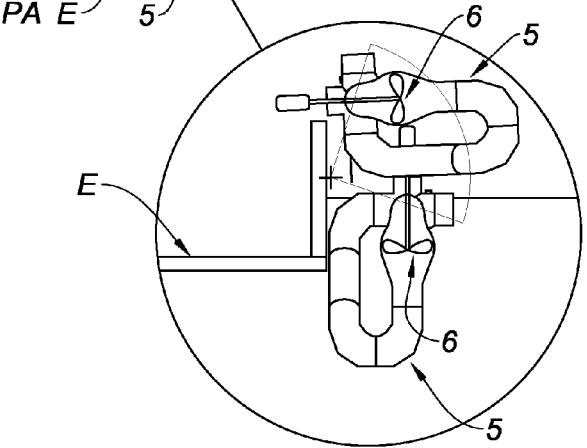
FIG. 9c is an enlarged view of an area of FIG. 9b, illustrating the pipe in two distinct positions, namely a raised position and a lowered position.
Figure 10:
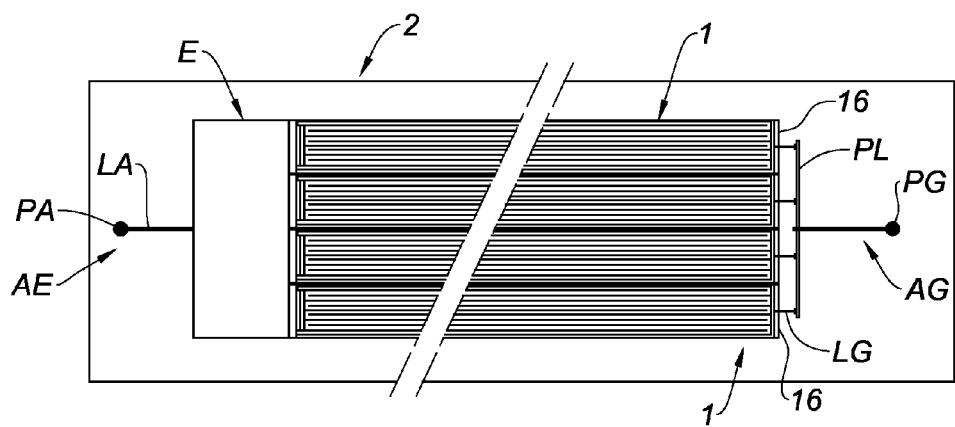
FIG. 10 is a schematic top view of a reactor according to the invention including several casings secured on both sides respectively on a craft and a rubber bar system.

As shown in FIGS. 9 to 11, the closing pipe 5 and the circulation means 6 are fixed on a craft E resting on the water; this craft E may be of the floating type and form a floating barge or craft, or may be of the pontoon type with beams or planks planted on the bottom of the expanse of water.

This craft E may comprise a closed space, or technical space, in which are disposed, sheltered from bad weather, the closing pipe 5 and circulation means 6, and a wall or freeboard FB on which the closing pipe 5 is fixed.

As shown in FIGS. 9 to 11, the craft E floats and is moored to the bottom of the expanse of water, herein shallow, by a single mooring AE of the craft E, in such a manner that the casing or casings 1 can align in the current field induced by the wind from the craft E freely oscillating around its single mooring AE. This mooring AE includes a mooring point PA, achieved in particular, in the form of a beam or rod planted vertically on the bottom of the expanse of water, and mooring links LA linking the craft E to the mooring point PA and leaving said craft E free to rotate around the mooring point PA. When the mooring AE is done in a single point, enough space must be provided so that the assembly can rotate around this point under the influence of the currents and wind.

In a first embodiment shown in FIGS. 9a and 9b, the downstream lateral edge 16 of the casing 1 is let free, thus allowing the casing 1 to align in the direction of the relative displacement of the mass of water which supports the assembly, and has the effect of reducing drag forces related to displacement of this support water mass.

In a second embodiment shown in FIG. 10 the lateral downstream edge 16 of the casing 1 is moored to the bottom of the expanse of water, here shallow, by a mooring AG, in such a manner that the casing 1 can no longer be aligned in the current field induced by the wind.

This mooring AG comprises links LG connecting the downstream lateral edges 16 of the casing 1 to a rudder PL perpendicular to the cells 33, 34, and a mooring point PG achieved in particular, in the shape of a beam or rod planted vertically in the bottom of the expanse of water, to which the rudder PL is connected. The adjustment of the length of the links LG and their parallel disposition allows to uniformly distribute the mooring tensions uniformly between all casings 1.

In case the water is navigable, diurnal and nocturnal signaling means in accordance with local legislations may equip the different points of this floating assembly, and in particular, the downstream lateral edges 16 of the casings 1.

Figure 11A:
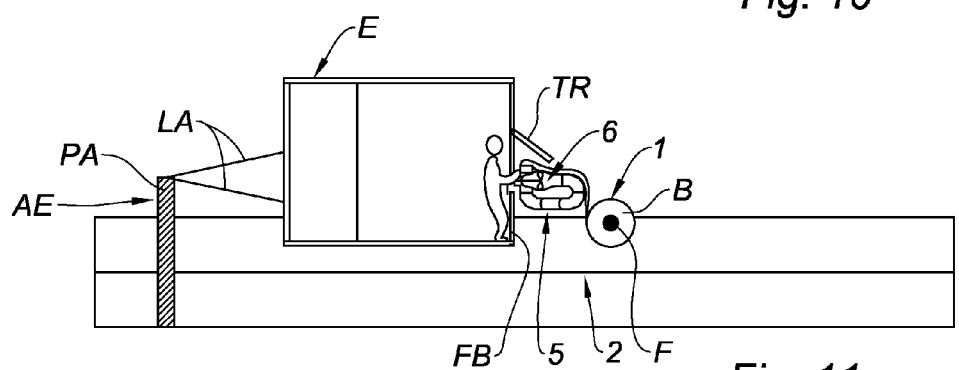
FIGS. 11a and 11b are schematic side views of a reactor according to the invention including a casing secured on one side on a floating craft, respectively illustrating a step of setting-up the casing on the closing pipe and a step of deployment of the casing on the water body by inflation or filling.
Figure 11B:
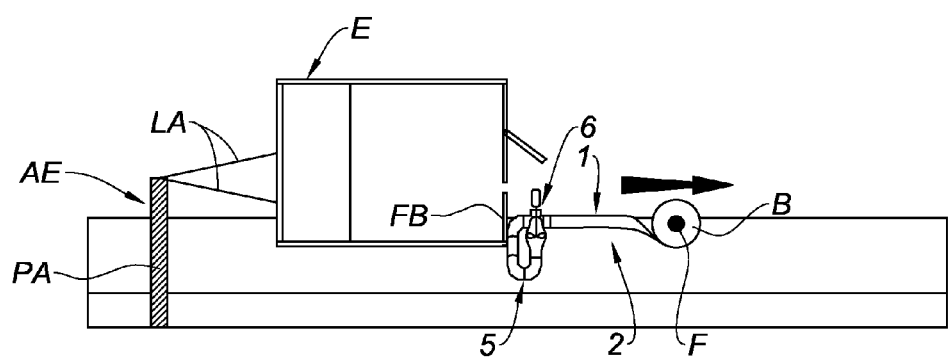

Furthermore, and as illustrated in FIG. 9c and in FIGS. 11a and 11b, the closing pipe 5 may be partly movable in a raised position in order to be able to come out of the water, in order to allow in particular, of the placing of the casing 1 out of the water and under aseptic conditions.

The placement of the casing 1 is described hereinafter with reference to FIGS. 11a and 11b. The casing 1 can be delivered in the form of bobbins B, where the floating mandrel F is positioned at the center of the bobbin B in order to stabilize it when afloat on the expanse of water.

As shown in FIG. 11a, the two openings 11, 12 of the casing 1 are hermetically connected on the closed pipe 5; said closing pipe 5 advantageously occupying a raised position. This operation of attaching the casing 1 on the closing pipe 5 is done aseptically to avoid introducing contaminants into the culture medium.

As shown in FIG. 11b, the closing pipe 5 is lowered and partly immersed in water, then the deployment of the casing 1 is carried out by filling by means of sterile liquid L and gaseous G media; traction on the floating mandrel F may possibly facilitate the smooth deployment.

Once the casing 1 is unwound and inflated, the circulation of the liquid medium L can be established in the reactor 2, by starting up the circulation means 6. The gas circulation in the casing 1 creates positive buoyancy distributed homogeneously along the length of the casing 1 which maintains them at the surface. The horizontality is ensured naturally by the sustenance of the expanse of water and by the gas circulation. A hatch TR may be provided on the craft E to isolate the outer portion of the reactor 2 from the inner portion of the reactor 2 once the casing 1 is unwound and inflated.

In the embodiments illustrated in the figures, the closing pipe 5 and circulation means 6 are disposed outside the craft E, this is known as a solution called "outboard". It is of course possible that the closing pipe 5 exhibits an inner portion, disposed inside the craft E with the circulation means 6 advantageously disposed in this inner portion, and an outer portion disposed outside the craft E and connected to the casing 1; This is known as a solution called "inboard". In this "inboard" solution, it is possible to allow the outer portion of the closing pipe 5 to be movable with respect to the inner portion in a raised position in order to be able to get it out of the water.

Figure 8:
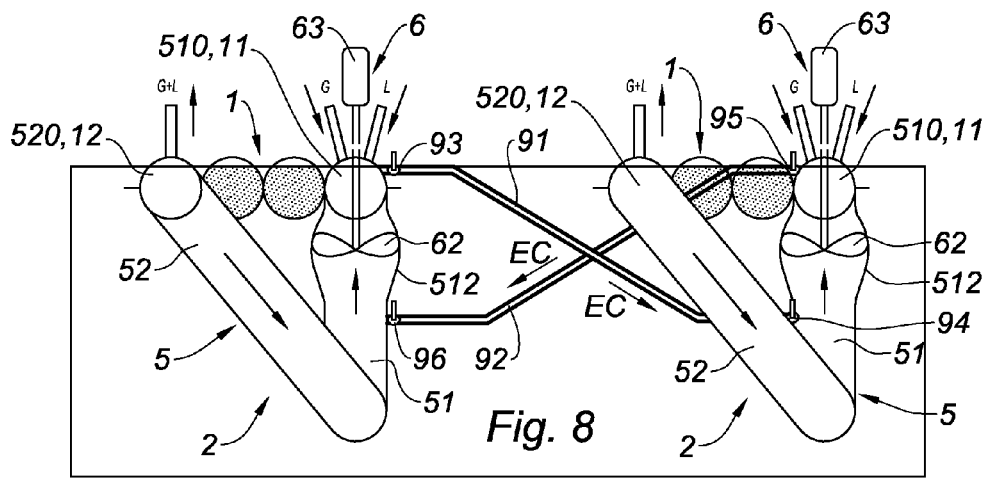
FIG. 8 is a schematic cross-sectional view of two reactors according to the invention connected together via connection pipes.

As illustrated in FIG. 8, the invention also relates to an assembly of photosynthetic reactors comprising at least two reactors 2 in accordance with the invention, namely a first (left) and second (right) reactor, and comprising at least one connection pipe 91, 92 ensuring fluid connection between the first reactor and the second reactor and least one valve 93, 94, 95, 96 disposed on said connection pipe 91, 92 to allow the inoculation of one reactor by the other reactor. It is thus, possible to interconnect two reactors in such a manner that their contents are exchanged, in order to allow a possible inoculation of one reactor by another, the concentration of which would have reached an advanced stage.

In the embodiment illustrated in FIG. 8, the assembly includes two connection pipes 91, 92 between the two reactors 2. The connection pipes 91, 92 are provided, at their respective ends, with valves respectively 93, 94 for the connection pipe 91 and respectively 95, 96 for the connection pipe 92.

The first connection pipe 91 links:
an inlet point disposed on the first reactor 2 downstream of the circulation means 6, such that the rotating propeller 62, in the high portion 510 of the ascending portion 51; to
an outlet point disposed on the second reactor 2 upstream of the circulation means 6 of this second reactor 2, in the low portion 511 of the ascending portion 51.

The second connecting pipe 92 links:
an inlet point disposed on the second reactor 2 downstream of the circulation means 6, in the high portion 510 of the ascending portion 51; to
an outlet point disposed on the first reactor 2 upstream of the circulation means 6 of this second reactor 2, in the low portion 511 of the ascending portion 51.

The reactors 2 are assembled in a parallel manner to form a coherent and productive assembly. In order to make the inoculation of a reactor by its neighbor possible, the microorganism concentration of which would have reached an advanced stage, the assembly allows the interconnection of these two reactors with the connection pipes 91, 92 such that their respective contents are mixed. Furthermore, the outlet points of the connection pipes 91, 92 are placed at the end of the convergence areas upstream of the corresponding housing 512 to benefit from a Venturi effect.

The valves 93, 94, 95, 96 allow the aseptic connection of the two connection pipes 91, 92 which connect crosswise and symmetrically the inlet points and outlet points of the two reactors 2 to be interconnected. The valves 93, 94, 95, 96 are substantially disposed at inlet and outlet points of the corresponding connection pipes 91, 92.

The use of such an assembly can be done in the following manner in order to proceed with the inoculation of the second reactor 2 (right) from the first reactor 2 (left) already in service when the concentration of microorganisms has reached the level of exploitation.

First, the valves 93, 94 and their counterparts 95, 96 are closed, the first reactor 2 is in operation with the establishment of the circulation inside this first reactor, and the second reactor 2 to be inoculated is filled with a sterile nutritive medium. Second, the circulation is established inside the second reactor 2 and the valves 93, 94 and their counterparts 95, 96 are opened to establish a cross exchange between the two reactors as illustrated by the arrows EC in FIG. 8. The interconnection between the two reactors 2 is established between the upstream and downstream of the circulation means 6 so that the propulsive force obtained with these circulation means 6 promotes the exchange circulation. After the opening of the valves 93, 94 and their counterparts 95 96, the concentrations become substantially equal in both reactors 2 and they can both be isolated by closing the valves 93, 94 and their counterparts 95, 96. To reduce the duration of this exchange, a pump (not visible) may be interposed on one and/or the other of the connection pipes 91, 92.

As illustrated schematically in FIGS. 9a and 10, the invention also relates to a reactor 2 including a plurality of reaction casings 1 connected in a parallel manner, this reactor 2 may comprise a single closing pipe (not visible) in which is disposed a unique circulation means for the assembly of casings 1. In this particular embodiment, which comprises interconnecting reaction casings 1 in series or in parallel, so that certain functionalities are shared, such as circulation means and regulation means?

In a parallel configuration, the closing pipe comprises a collecting duct in which circulation means is disposed, and a plurality of distribution ducts connected, on one hand, to the collecting duct and, on the other hand, to the respective casings 1, such that the liquid medium is collected at the outlet of casings 1, passes through the circulation means and then is distributed at the inlet of the casings 1.

In a series configuration, the second opening 12 (outlet of the liquid medium) of a casing 1 is directly connected to the first opening 11 (inlet of the liquid medium) of the following casing 1, and the closing pipe is disposed between the first opening 11 of the first casing and the second opening 12 of the last casing.

In the parallel configuration, the cleaning efficiency is however, not optimal as the cleaning elements are distributed randomly in the casings 1. That is why a series configuration is preferred where the cleaning elements must follow a single path, from casing to casing.

The method for cultivating photosynthetic microorganisms, in particular algae, using a reactor 2 in accordance with the invention comprises the following steps:
injecting a liquid culture medium L in the reaction casing 1 according to a flow rate controlled by the liquid injection means 71;
injecting gas G in the reaction casing 1 according to a flow rate controlled by the gas injection means 72;
pressurizing the casing 1 comprising creating an inflation overpressure in this casing 1 to ensure the buoyancy and the deployment thereof;
circulating the liquid culture medium with the circulation means 6;
controlling the circulating means 6 and the gas injection means 72 in order to establish in the reaction casing 1 a two-phase gas/liquid culture medium flow regime of the stratified flow or of the slug or elongated bubbles flow type; and recovering photosynthetic microorganisms with the liquid outlet means 81.

During the travel in the casing 1, the liquid medium containing the photosynthetic microorganisms receives solar radiation through the transparent material of the membranes 31, 32 of the casing 1, exchanges heat with the body of water by diffusion, mixture and conduction through this same material, and exchanges components with the gas G through their common interface. The production capacity mainly depends on the length of the casing 1 and the number of cells 33, 34.

Advantageously, the circulation velocity of the liquid in the casing 1 ranges between 0.1 and 1.0 m/s.

Furthermore, the circulation velocity of the gas is established between about 0.5 and 2.0 m/s, corresponding to an adequate velocity regime for the flow rates required for the reaction.

Still more advantageously, the circulation means 6 comprising a propeller 62 driven in rotation by a motor 63 is controlled in such a manner that the speed of rotation of the propeller 62 is less than about 1000 rpm, in order to limit the mechanical stresses within the liquid culture medium.

The invention also relates to a method for manufacturing a casing 1 according to the first assembly mode or the second assembly mode (described hereinafter) and comprising the following steps:

providing an upper membrane 31 and a lower membrane 32 made at least partially from a material which is flexible, watertight and transparent to light radiation;

covering the lower membrane 32 with the upper membrane 31;

hermetically connecting the two membranes 31, 43 according to junction lines 41, 42 alternately delimiting inflatable cells 33, 34 and inflatable junction elbows 35, 36 pairwise joining the cells 33, 34 to define a flow path with a globally sinuous form between the two openings 11, 12, the two openings 11, 12 being provided at the ends of this path; and winding the casing 1 around a drum to form a bobbin B.

In the first assembly mode described hereinabove with reference to FIGS. 1 to 4, the casing 1 is made from the only membranes 31, 32 which are assembled together along to the junction lines, and two embodiments are possible.

In a first embodiment of the first assembly mode of the casing 1, the two membranes 31, 32 are composed of two sheets (otherwise known as films), distinct and separated from one another before assembly, the assembly consisting afterwards in interconnecting them thanks to the junction lines 41, 42, 47. In this embodiment, the lower membrane 32 is not necessarily transparent to solar radiation, solely the upper membrane 31 should imperatively be transparent.

In a second embodiment of the first assembly mode, the two membranes 31, 32 are composed of one and the same sheet 5 (otherwise known as film) which is folded in two in the direction of its length along a longitudinal folding line, then the junction lines 41, 42, 47 are made to hermetically connect both sides of the sheet and thereby form the casing 1; the longitudinal folding line can possibly constitute a junction line 41.

In a second assembly mode described with reference to FIG. 12, the casing 1 is composed of three distinct portions, namely an upstream portion 100, a downstream portion 101 and a central portion 102 interposed between the two end portions 100 and 101.

The upstream portion 100 is composed of an assembly of an upper skin (otherwise known as sheet or film) and a lower skin hermetically connected to each other along junction lines 41, 42, 47 in order to delimit both the upstream portions 330, 340 of the cells 33, 34 and the upstream junction elbows 35, the two openings 11, 12 being provided in this upstream portion 100.

The downstream portion 101 is composed of an assembly of an upper skin and a lower skin hermetically connected to each other along junction lines 41, 42, 47 in order to delimit both the downstream portions 331, 341 of the cells 33, 34 and the downstream junction elbows 36.

The central portion 102 is composed of an assembly of an upper skin and a lower skin hermetically connected to each other along junction lines 41 in order to delimit only central portions 332, 342 of the cells 33, 34. The central portion 102 exhibits a length equivalent to at least 90% of the total length of the casing 1.

Thus, the three portions 100, 101, 102 are made independently from each other, then joined end to end to form the casing 1; the upper membrane 31 of the casing 1 comprising the assembly of the upper skins of these portions 100, 101, 102, while the lower membrane 32 of the casing 1 comprises the assembly of the lower skins of these portions 100, 101, 102. The end to end junction of these three portions 100, 101, 102 is performed so that the junction lines 41 of the various portions are aligned and continuous.

The main advantage of this embodiment with three portions is to facilitate the realization of the elbows 35, 36 to guarantee their geometries. In fact, it is important to respect the geometry described hereinabove for the elbows 35, 36, and in particular, the minimum width of the elbows 35, 36 in their respective planes of symmetry, which requires the control of the interruption of the junction lines 41 at their free ends 45, 46. When working with short end portions 100, 101, it is thereby easier to control the localization and the interruption of the junction lines 41 and guarantee the required geometry.

Furthermore, it is possible to choose skins that are not transparent to solar radiation in order to make the end portions 100 and 101, thus, allowing to possibly select more suitable materials for achieving bent junction lines 42 and interruptions in the rectilinear junction lines 41 Only the central portion 102 must be made of a material transparent to solar radiation, or even only the upper skin of the central portion 102 must be made from a material transparent to solar radiation. The central portion 102 may be made by assembling two separate sheets, or by folding one same and single sheet.

In the embodiments described above with reference to FIGS. 1 to 4 and 12, each cell 33, 34 is separated from the adjacent cell or cells by one single junction line 41.

Figure 13A:
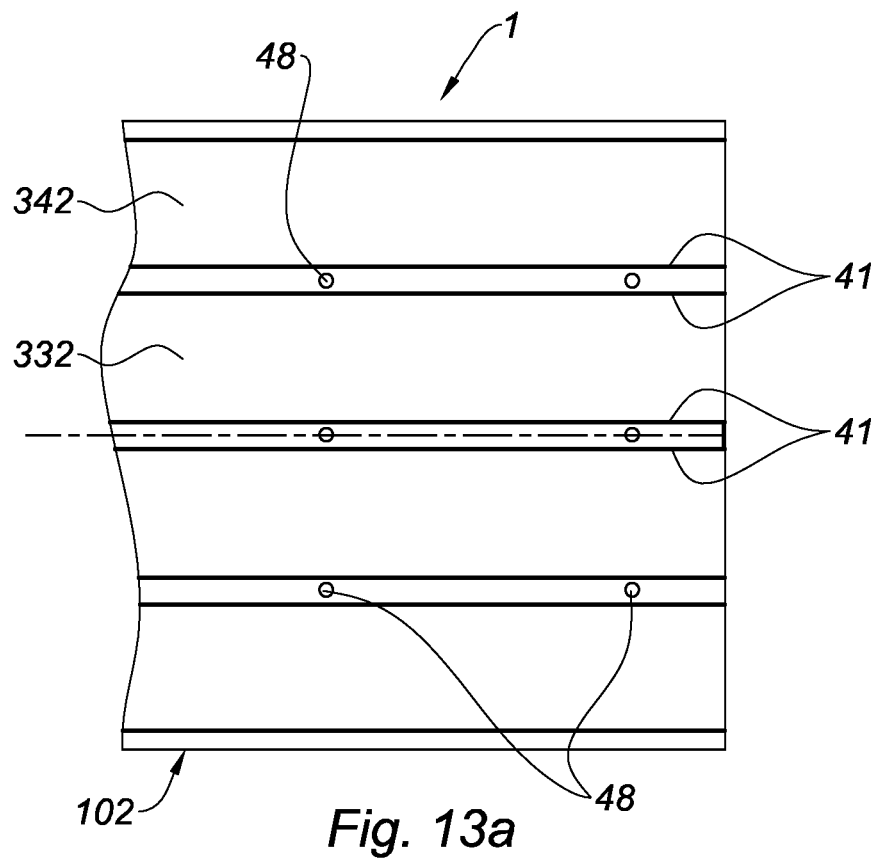
FIG. 13a is a schematic top view of a variant of the central portion of the casing of FIG. 12.
Figure 13B:
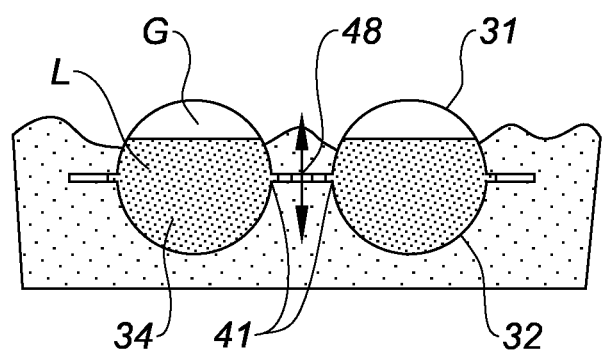
FIG. 13b is a schematic cross-sectional partial view of the variant of the central section of FIG. 13a after inflation.

In a variant alternative shown in FIGS. 13a and 13b, each cell 33, 34 is separated from the adjacent cell or cells by two junction lines 41, parallel and spaced apart from one another. This doubling of junction lines 41 between the cells 33, 34 can be considered with the casing 1 of the first assembly mode, or with the casing 1 of the second assembly mode where each portion 100, 101, 102 exhibits a duplication of these junction lines 41 between the portions 330, 340, 331, 341, 332, 342 of the cells 33, 34. In this case, it is possible to provide holes 48 in the casing 1 between the two paired junction lines 41 (obviously not in the cells 33, 34), in order to allow the water flow through these holes 48 once casing 1 becomes inflated and floating on the water surface.

In a third assembly method described with reference to FIGS. 14a and 14b, the casing 1 comprises rigid junction elbows 35, 36 which are hermetically attached to the ends of the inflatable cells 33, 34.

Figure 12:
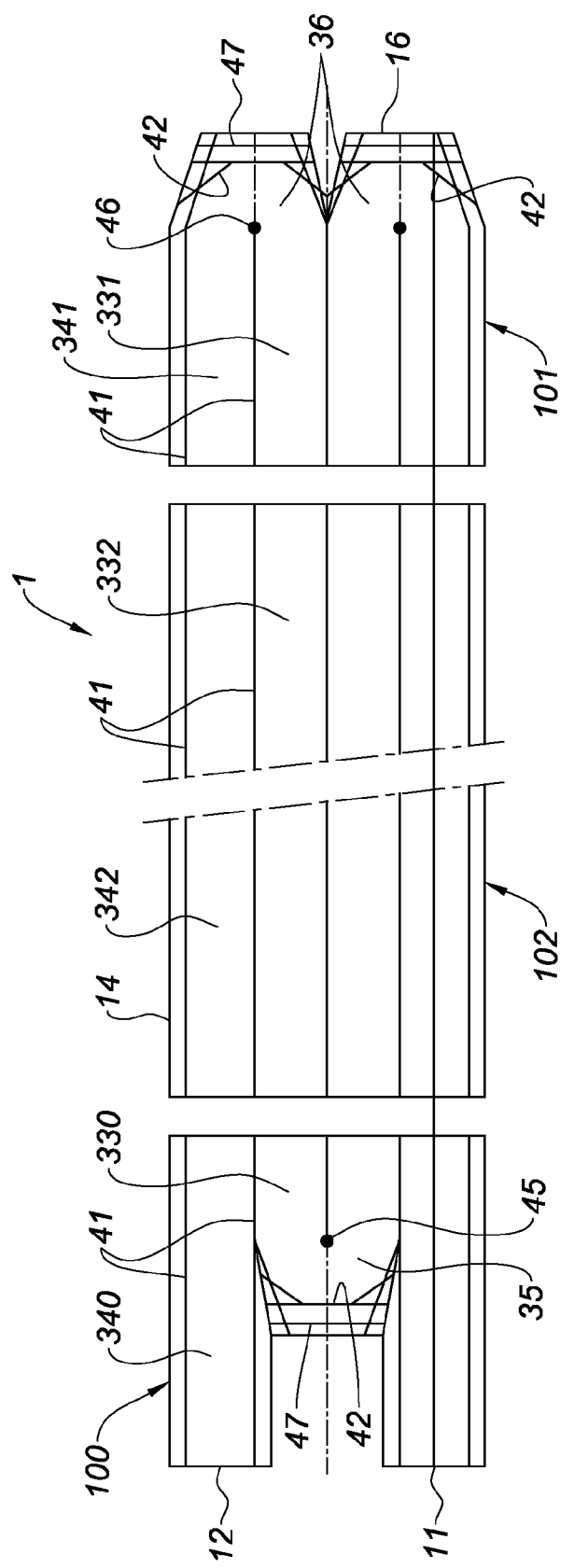
FIG. 12 is a schematic top view of a reaction casing according to the invention, according to a second assembly mode, before the end-to-end junction of three distinct portions composing it, including a central portion and two end portions.

In the assembly method illustrated in FIGS. 14a and 14b, the casing 1 is composed of a central portion 102 of the same type as that of FIG. 13a or of FIG. 12, which is composed of an assembly of an upper skin and a lower skin hermetically connected to each other along junction lines 41 (either single or double) for the cells 33, 34.

To report the rigid elbows 35, 36, the latter preferably exhibit nozzles 350, 360 which are introduced inside the ends of the cells, and then pipe clamps 351, 361 are tightened around these nozzles 350, 360 to guarantee permeability.

Likewise, stiff inlet 37 and outlet 38 ducts maybe attached to the openings 11, 12 of the casing 1; these rigid inlet 37 and outlet 38 ducts preferably exhibiting nozzles 370, 380 which are introduced inside the openings 11, 12, then pipe clamps 371, 381 are tightened around these nozzles 370, 380 to guarantee a permeability.

Furthermore, it may be considered stiff downstream junction elbows 36 be gathered within one same stiff downstream piece 391 and that the stiff upstream junction elbows 35 and the stiff ducts 37, 38 be gathered within a same rigid upstream piece 390.

Of course, the aforementioned implementation example does not exhibit any limiting nature and other improvements and details may be attached to the casing, reactor and methods according to the invention, without nevertheless departing from the scope of the invention where other forms of membrane and/or cell and/or the junction elbow and/or the closing pipe can for example be carried out.

The invention claimed is:

1. A reaction casing for a photosynthetic reactor suitable for cultivating photosynthetic microorganisms said reaction casing being designed to float on an expanse of water and to delimit a two-phase flow pathway for a gas/liquid culture medium between a first and second opening of said reaction casing, said reaction casing comprising, an upper membrane and a lower membrane made at least partially from a material that is flexible, watertight and transparent to light radiation, said membranes being hermetically connected along junction lines delimiting adjacent inflatable cells and, on the other hand, junction elbows pairwise joining said cells to define said flow path of generally sinuous shape, one of the cells being in fluid connection with the first opening and another cell being in fluid connection with the second opening, wherein the junction elbows are inflatable junction elbows and are made at least partially from a flexible and watertight material, wherein the casing is composed of three distinct portions comprising an upstream portion, a downstream portion and a central portion interposed between the upstream and downstream portions, wherein:

the upstream portion is composed of an assembly of an upper skin and a lower skin hermetically connected to each other along junction lines in order to delimit both upstream portions of the cells and upstream inflatable junction elbows, the two openings being provided in this upstream portion;

the downstream portion is composed of an assembly of an upper skin and a lower skin hermetically connected to each other along junction lines in order to delimit both downstream portions of the cells and downstream inflatable junction elbows; and the central portion is composed of an assembly of an upper skin and a lower skin hermetically connected to each other along junction lines in order to delimit only the central portions of the cells.

2. The casing of claim 1, wherein the cells comprise a several pairs of cells, each pair of cells comprising:

a departure cell defining a circulation of the liquid culture medium from an upstream portion of the casing to a downstream portion of the casing, where one of the departure cells is in fluid connection with the first opening disposed in the upstream portion of the casing; and a return cell defining a circulation of the liquid culture medium of said downstream portion towards said upstream portion, where one of the return cells is in fluid connection with the second opening disposed in the upstream portion of the casing; and wherein the junction elbows alternately include downstream junction elbows disposed in the downstream portion of the casing and upstream junction elbows disposed in upstream portion of the casing to join pairwise the departure and the return cells.

3. The casing according to claim 1, wherein each cell is delimited by two rectilinear junction lines to define a rectilinear portion of the flow path, wherein said rectilinear junction lines present free ends, and each inflatable junction elbow is delimited at least outwardly by a bent junction line substantially bent at 180° and exhibiting two ends connected to two rectilinear junction lines delimiting two adjacent cells.

4. The casing according to claim 3, wherein the ends of each bent junction line or the free ends of the rectilinear junction lines located inside corresponding inflatable junction elbows are provided with reinforcing elements hermetically crossing the two membranes.

5. The casing according to claim 3, wherein each bent junction line exhibits either an overall shape of a semicircle, or an overall shape of a broken line formed of several rectilinear segments.

6. The casing according to claim 1, wherein the casing is made up of only the upper and lower membranes, said membranes being hermetically connected to each other along junction lines alternately delimiting the inflatable cells and the inflatable junction elbows.

7. The casing according to claim 1, wherein the cells define rectilinear portions of the flow pathway which are parallel to a longitudinal direction of the casing and are of substantially equivalent lengths.

8. The casing according to claim 1, wherein the junction lines comprise at least one of welding, sewing, gluing or clipping lines between the two membranes.

9. A photosynthetic reactor suitable for the culture of photosynthetic microorganisms, comprising:

at least one reaction casing according to claim 1;

at least one closing pipe ensuring fluid connection between the first and second openings of said reaction casing;

at least one circulation device disposed in said closing pipe and designed to put into circulation the liquid culture medium in the closing pipe and the reaction casing;

at least one liquid injector disposed in said closing pipe and designed to allow injection of the liquid in the reaction casing;

at least one gas injector disposed in said closing pipe and designed to allow injection of the gas in the reaction casing;

at least one liquid outlet for harvesting the culture of photosynthetic microorganisms; and at least one gas exhaust disposed in said closing pipe and designed to allow the release of gas injected in the reaction casing.

10. The photosynthetic reactor according to claim 9, wherein the closing pipe exhibits a globally "U" or "V" shape and comprises:

an ascending portion provided with a high portion in fluid connection with the first opening; and a descending portion provided with a high portion in fluid connection with the second opening;

the descending portion and the ascending portion being provided with respective low portions in fluid connection, and the circulation device being designed for putting the liquid culture medium in circulation in the reaction casing from the first opening to the second opening.

11. The photosynthetic reactor according to claim 10, wherein the liquid injector is disposed in the high portion of the ascending portion, and the gas injector is disposed in the ascending portion, in the high portion or the low portion of said ascending portion.

12. The photosynthetic reactor according to claim 11, wherein the circulation device is constituted of a gas lift device and comprises a gas injection duct disposed in the low portion of the ascending portion, said gas injection duct also constituting the gas injecting injector.

13. The photosynthetic reactor according to claim 11, wherein the gas exhaust and the liquid outlet are constituted of a common duct disposed in the high portion of the descending portion, said common duct being provided with a free end set at an adjustable height with respect to the expanse of water.

14. The photosynthetic reactor according to claim 11, wherein the gas exhaust is constituted of a first outlet duct disposed in the high portion of the descending portion, and the liquid outlet is constituted of a second outlet duct disposed in the low portion of either one of the ascending or descending portions and provided with a free end set at an adjustable height with respect to the expanse of water.

15. The photosynthetic reactor according to claim 10, wherein the liquid injector is disposed in the high portion of the ascending portion, and the gas injector is disposed in the descending portion, and wherein the gas exhaust is constituted of a first outlet duct disposed in the high portion of the ascending portion and the liquid outlet is constituted of a second outlet duct disposed either in the high portion of the descending portion or in the low portion of either one of the ascending or descending portions, said second outlet duct being provided with a free end set at an adjustable height with respect to the expanse of water.

16. The photosynthetic reactor according to claim 10, wherein the circulation device is constituted of a mechanical circulation device, said mechanical circulation device being disposed in the ascending portion.

17. A method for manufacturing a reaction casing according to claim 1, comprising the following steps:

providing an upper membrane and a lower membrane achieved at least partially of a material that is flexible, watertight and transparent to light radiation;

hermetically connecting said membranes along junction lines delimiting the inflatable cells; and providing inflatable junction elbows made at least partially from a flexible and watertight material and joining pairwise said cells to define a flow pathway of generally sinuous shape between a first opening and a second opening provided in said casing, wherein the casing is composed of three distinct portions comprising an upstream portion, a downstream portion and a central portion interposed between the upstream and downstream portions, wherein:

the upstream portion is composed of an assembly of an upper skin and a lower skin hermetically connected to each other along junction lines in order to delimit both upstream portions of the cells and upstream inflatable junction elbows, the two openings being provided in this upstream portion;

the downstream portion is composed of an assembly of an upper skin and a lower skin hermetically connected to each other along junction lines in order to delimit both downstream portions of the cells and downstream inflatable junction elbows; and the central portion is composed of an assembly of an upper skin and a lower skin hermetically connected to each other along junction lines in order to delimit only the central portions of the cells.

18. A photosynthetic microorganism cultivation method, using a reactor according to claim 9, and comprising the following steps:

injecting a liquid culture medium in the reaction casing according to a flow rate controlled with the liquid injector;

injecting a gas into the reaction casing according to a flow rate controlled with the gas injector;

circulating the liquid culture medium with the circulation device;

controlling the circulation device and the gas injector in order to establish in the reaction casing a two-phase gas/liquid culture medium flow regime.

19. The method according to claim 18, wherein the controlling step comprises a step of controlling the velocity of the circulation of the liquid in the reaction casing between 0.1 and 1.0 m/s, and a step of controlling the velocity of circulation of the gas in the reaction casing between 0.5 and 2.0 m/s.

* * * * *